US012745729B2

(12) United States Patent
Bennett

(10) Patent No.: US 12,745,729 B2
(45) Date of Patent: Sep. 29, 2026

(54) **PLANTS AND SEEDS OF *BRASSICA CARINATA* HYBRID VARIETY NUJET 400**

(71) Applicant: Nuseed Global Innovation Ltd., Manchester (GB)

(72) Inventor: Rick Bennett, Saskatoon (CA)

(73) Assignee: Nuseed Global Innovation Ltd., Manchester (GB)

( * ) Notice: Subject to any disclaimer, the term of this patent is extended or adjusted under 35 U.S.C. 154(b) by 218 days.

(21) Appl. No.: 18/488,356

(22) Filed: Oct. 17, 2023

(65) Prior Publication Data

US 2024/0138332 A1 May 2, 2024

Related U.S. Application Data

(60) Provisional application No. 63/419,863, filed on Oct. 27, 2022.

(51) Int. Cl.
*A01H 5/10* (2018.01)
*A01H 6/20* (2018.01)

(52) U.S. Cl.
CPC ................. *A01H 6/20* (2018.05); *A01H 5/10* (2013.01)

(58) Field of Classification Search
None
See application file for complete search history.

(56) References Cited

U.S. PATENT DOCUMENTS

2018/0042266 A1 2/2018 Hetherington
2020/0315117 A1* 10/2020 Bennett .................... A01H 5/12

FOREIGN PATENT DOCUMENTS

WO 2017091891 A1 6/2017

OTHER PUBLICATIONS

USDA, "Applying for a Plant Variety Certificate of Protection", https://www.ams.usda.gov/services/pvpo/application-help/apply, accessed May 1, 2023.*
UPOV, 2017, Explanatory Notes on Essentially Derived Varieties Under the 1991 Act of the UPOV Convention.*
Ex Parte C (USPQ 2d 1492 (1992).*
Ex Parte McGowen—Board Decision in U.S. Appl. No. 14/996,093. (Year: 2020).*
Huan et al. Plant Physiology. 155:645-655. (Year: 2011).*
Großinsky et al. Journal of Experimental Botany. 66(18):5429-5440. (Year: 2015).*
Newman, Noah. "New Cover Crop Offers Profitability Potential in the South". No-Till Farmer. May 2022. https://www.no-tillfarmer.com/articles/11570-new-cover-crop-offers-profitability-potential-in-the-south; accessed Jul. 18, 2025. (Year: 2022).*
Applicant's admission in IDS filed Sep. 17, 2024 states that *Brassica carinata* variety Nujet 400 was first offered for sale in Paraguay in Nov. 2021; seller was not indicated in IDS.*
*Brassica carinata* variety NuJet 400 first offered for sale in Paraguay in Nov. 2021.
Alcántara C., et al. (2011). "Management of cruciferous cover crops by mowing for soil and water conservation in southern Spain." Agricultural Water Management 98(6): 1071-1080.
Angus, J., et al. (2011). "A review of break-crop benefits of brassicas". 17th Australian Research Assembly on Brassicas, Wagga Wagga, NSW, Aug. 2011. Wagga Wagga, NSW, NSW DPI: 123-127.
Babic, V., et al. (1998). "Development of an efficient Agrobacterium-mediated transformation system for *Brassica carinata*." Plant Cell Reports 17(3): 183-188.
Bannerot, H., et al. (1977). "Unexpected Difficulties Met With the Radish Cytoplasm in *Brassica oleracea*." Cruciferae Newsl 2: 1.
Barro, F. and Martin, A. 1999, "Response of different genotypes of *Brassica carinata* to microspore culture", Plant Breeding 118 (1): 79-81.
Bevan, M. (1984). "Binary Agrobacterium vectors for plant transformation." Nucl. Acids Res. 12(22): 8711-8721.
Black, C. K. and Panozzo, J.F. (2004). "Accurate Technique for Measuring Color Values of Grain and Grain Products Using a Visible-NIR Instrument." Cereal Chemistry 8(14): 469-474.
Bouaid, A., et al. 2005). "Pilot plant studies of biodiesel production using *Brassica carinata* as raw material." Catalysis Today 106(1-4): 193-196.
Cardone, M., et al. (2003). "Brassica carinata as an alternative oil crop for the production of biodiesel in Italy: agronomic evaluation, fuel production by transesterification and characterization." Biomass and Bioenergy 25(6): 623-636.
Cardone, M., et al. (2002). "*Brassica carinata* as an alternative oil crop for the production of biodiesel in Italy: engine performance and regulated and unregulated exhaust emissions." Environ Sci Technol 36(21): 4656-4662.
Cheng, B., et al. (2010). "Towards the production of high levels of eicosapentaenoic acid in transgenic plants: the effects of different host species, genes and promoters." Transgenic Research 19(2): 221-229.
Dalta, R. S., et al. (1992). "Modified binary plant transformation vectors with the wild-type gene encoding NPTII." Gene 122(2): 383-384.
Delourme, R., et al. (1991). "Radish cytoplasmic male sterility in rapeseed: breeding restorer lines with a good female fertility". Eighth International Rapeseed Congress, Saskatoon, Canada, 1506-1510.
Delourme, R., et al. (1998). "Characterisation of the radish introgression carrying the Rfo restorer gene for the Ogu-INRA cytoplasmic male sterility in rapeseed ( *Brassica napus* L.)." TAG Theoretical and Applied Genetics 97(1-2): 129-134.
Drenth, A. C., et al. (2015). "Fuel property quantification of triglyceride blends with an emphasis on industrial oilseeds camelina, carinata, and pennycress." Fuel 153: 19-30.

(Continued)

*Primary Examiner* — David R Byrnes
(74) *Attorney, Agent, or Firm* — Harness, Dickey & Pierce, P.L.C.

(57) ABSTRACT

The invention is in the field of *Brassica carinata* breeding (i.e. Ethiopian mustard breeding), specifically relating to *Brassica carinata* variety Nujet 400. The present invention relates to seeds, plants or parts thereof, cells, methods of making, and uses of this variety and its progeny.

14 Claims, No Drawings

(56) References Cited

OTHER PUBLICATIONS

Finer, J. J., et al. (1999). "Particle bombardment mediated transformation." Curr Top Microbiol Immunol 240: 59-80.
Fromm, M., et al. (1985). "Expression of genes transferred into monocot and dicot plant cells by electroporation." Proc. Natl. Acad. Sci. USA 82(17): 5824-5828.
Gasol, C., et al. (2007). "Life cycle assessment of a Brassica carinata bioenergy cropping system in southern Europe" Biomass and Bioenergy 31(8): 543-55.
Gasol C. M., et al. (2009). "Feasibility assessment of poplar bioenergy systems in the Southern Europe." Renewable and Sustainable Energy Reviews 13(4): 801-812.
Gesch, R. W., et al. (2015). "Comparison of several *Brassica* species in the north central U.S. for potential jet fuel feedstock." Industrial Crops and Products 75b: 2-7.
Getinet, A., et al. (1996). "Agronomic performance and seed quality of Ethiopian mustard in Saskatchewan." Canadian J Plant Sci. 76(3): 87-392.
Getinet, A., et al. (1997). "Glucosinolate content in interspecific crosses of *Brassica carinata* with *B.juncea* and *B. napus*." Plant Breeding 116(1): 39-46.
Gleba, Y., S. Marillonnet and V. Klimyuk (2004). "Engineering viral expression vectors for plants: the 'full virus' and the 'deconstructed virus' strategies." Curr Opin Plant Biol 7(2): 182-188.
Heyn, F. W. (1976). "Transfer of restorer genes from Raphanus to cytoplasmic male sterile *Brassica napus*." Cruciferae Newsl 1: 15-16.
Heyn, F. W. (1978). "Cytoplasmic Genetic-Male Sterility in *Brassica napus*." Cruciferae Newsl 3: 34-35.
Impallomeni, G., et al. (2011). "Synthesis and characterization of poly(3-hydroxyalkanoates) from *Brassica carinata* oil with high content of erucic acid and from very long chain fatty acids." International Journal of Biological Macromolecules 48(1): 137-145.
Jadhav, A., et al. (2005). "Increased levels of erucic acid in *Brassica carinata* by co-suppression and antisense repression of the endogenous FAD2 gene." Metab Eng 7(3): 215-220.
Jeffs, K. A., Ed. (1978). Seed treatment / compiled and edited by K.A. Jeffs. Monographs (Collaborative International Pesticides Analytical Council) ; 2. Harpenden : Cambridge (King's Hedges Rd, Cambridge CB4 2PQ), Collaborative International Pesticides Analytical Council ; [Distributed by] Heffers Printers Ltd.
Johnson, C. M. ,et al. (1989). "Direct gene transfer via polyethylene glycol." Methods in Cell Science 12(4): 127-133.
Kirkegaard, J. A. and Sarwar, M. (1998). "Biofumigation potential of brassicas." Plant and Soil 201(1): 71-89.
Lazzeri, L., et al. (2009). "On Farm Agronomic and First Environmental Evaluation of Oil Crops for Sustainable Bioenergy Chains." Ital. J. Agron. / Riv. Agron. 4: 171-180.
Marquez-Lema, A., et al. (2008). "Development and characterisation of a *Brassica carinata* inbred line incorporating genes for low glucosinolate content from *B. juncea*." Euphytica 164(2): 365-375.
Meier, U., et al. (2009). "The BBCH system to coding the phenological growth stages of plants—history and publications—." Journal Für Kulturpflanzen 61(2): 41-52.
Miki, B. L., et al. (1990). "Transformation of *Brassica napus* canola cultivars with *Arabidopsis thaliana* acetohydroxyacid synthase genes and analysis of herbicide resistance." Theor Appl Genet 80(4): 449-458.
Mnzava, N.A. & Schippers, R.R., 2007. "*Brassica carinata* A.Braun." [Internet] Record from PROTA4U. van der Vossen, H.A.M. & Mkamilo, G.S. (Editors). PROTA (Plant Resources of Tropical Africa / Ressources végétales de l'Afrique tropicale), Wageningen, Netherlands. 15 pages.
Mourato, M. P., et al. (2015). "Effect of Heavy Metals in Plants of the Genus *Brassica*." Int J Mol Sci 16(8): 17975-17998.
Nagaharu, U. (1935). "Genome analysis in *Brassica* with special reference to the experimental formation of *B. napus* and peculiar mode of fertilization." Japanese J. of Botany 7: 389-452.
Neugart, S., et al. (2017). "Indigenous leafy vegetables of Eastern Africa—A source of extraordinary secondary plant metabolites." Food Research International 100: 411-422.
Newman, Y. C., et al. (2010 (revised)). Cover Crops. I. Extension and U. o. Florida.
Newson, W. R., et al. (2014). "Effect of additives on the tensile performance and protein solubility of industrial oilseed residual based plastics." J Agric Food Chem 62(28): 6707-6715.
Ogura, H. (1968). "Studies on the New Male-Sterility in Japanese Radish, with Special Reference to the Utilization of this Sterility towerds the Practical Raising of Hybrid Seeds." Memoirs of the Faculty of Agriculture, Kagoshima University 6(2): 39-78.
Pane, C., et al. (2013). "Screening of plant-derived antifungal substances useful for the control of seedborne pathogens." Archives of Phytopathology and Plant Protection 46(13): 1533-1539.
Pellan-Delourme, R. and Renard, M. (1988). "Cytoplasmic male sterility in rapeseed (*Brassica napus* L.): female fertility of restored rapeseed with "Ogura" and cybrids cytoplasms." Genome 30(2): 234-238.
Pelletier, G., et al. (1983). "Intergeneric cytoplasmic hybridization in cruciferae by protoplast fusion." Molecular and General Genetics MGG 191(2): 244-250.
Pelletier, G., et al. (1987). "Molecular, phenotypic and genetic characterization of mitochondria1 recom-binants in rapeseed". Seventh International Rapeseed Conference: 113-118.
Petolino, J. F., et al. (2010). "Zinc finger nuclease-mediated transgene deletion." Plant Molecular Biology 73(6): 617-628.
Prakash, S.,et al. (2011). "History, Evolution, and Domestication of Brassica Crops". Plant Breeding Reviews, John Wiley & Sons, Inc.: 19-84.
Primard-Brisset, C., et al. (2005). "A new recombined double low restorer line for the Ogu-INRA cms in rapeseed (*Brassica napus* L.)." Theoretical and Applied Genetics 111(4): 736-746.
Rahman, M. and Tahir, M. (2010) "Inheritance of seed coat color of Ethiopian mustard (*Brassica carinata* A. Braun)", Can. J. Plant Sci. 90(3): 279-281.
Rothstein, S. J., et al. (1987). "Promoter cassettes, antibiotic-resistance genes, and vectors for plant transformation." Gene 53(2): 153-161.
Sauer, N. J., et al. (2016). "Oligonucleotide-Mediated Genome Editing Provides Precision and Function to Engineered Nucleases and Antibiotics in Plants." Plant Physiol 170(4): 1917-1928.
Seepaul, R., et al. (2015). "Carinata, the Jet Fuel Cover Crop": 2016 Production Recommendations for the Southeastern United States. Agronomy Department, IFAS Extension and U. o. Florida, University of Florida. SS-AGR-384: 1-8.
Sherwani, S. I., et al. (2015). Modes of Action of Different Classes of Herbicides. Herbicides, Physiology of Action, and Safety. A. Price, J. Kelton and L. Sarunaite. Rijeka, InTech: Ch. 08.
Tang, G. and G. Galili (2004). "Using RNAi to improve plant nutritional value: from mechanism to application." Trends Biotechnol 22(9): 463-469.
Taylor, D. C., et al. (2010). "Brassica carinata—a new molecular farming platform for delivering bio-industrial oil feedstocks: case studies of genetic modifications to improve very long-chain fatty acid and oil content in seeds." Biofuels, Bioproducts and Biorefining 4(5): 538-561.
Thompson, C. J., et al. (1987). "Characterization of the herbicide-resistance gene bar from Streptomyces hygroscopicus." The EMBO Journal 6(9): 2519-2523.
Tian, E., et al. (2014). "Molecular marker-assisted breeding for improved Ogura cms restorer line (RfoRfo) and mapping of the restorer gene (Rfo) in *Brassica juncea*." Molecular Breeding 34(3): 1361-1371.
Warwick, S. I., et al. (2009). "Guide to Wild Germplasm of *Brassica* and Allied Crops (tribe Brassiceae, Brassicaceae)": 302 pages.
Wohlleben, W., et al. (1988). "Nucleotide sequence of the phosphinothricin N-acetyltransferase gene from Streptomyces viridochromogenes Tu494 and its expression in Nicotiana tabacum." Gene 70(1): 25-37.
Woo, J. W., et al. (2015). "DNA-free genome editing in plants with preassembled CRISPR-Cas9 ribonucleoproteins." Nat Biotechnol 33(11): 1162-1164.

(56) References Cited

OTHER PUBLICATIONS

Xin, H. and Yu, P. (2014) "Rumen degradation, intestinal and total digestion characteristics and metabolizable protein supply of carinata meal (a non-conventional feed resource) in comparison with canola meal"., Animal Feed Sci Technol. 191: 106-110.
Zanetti, F., et al. (2013). "Challenges and opportunities for new industrial oilseed crops in EU-27: A review." Industrial Crops and Products 50: 580-595.
Zanetti, F., et al. (2009). "Yield and oil variability in modern varieties of high-erucic winter oilseed rape (*Brassica napus* L. var. *oleifera*) and Ethiopian mustard (*Brassica carinata* A. Braun) under reduced agricultural inputs." Industrial Crops and Products 30(2): 265-270.

* cited by examiner

PLANTS AND SEEDS OF *BRASSICA CARINATA* HYBRID VARIETY NUJET 400

CROSS-REFERENCE TO RELATED APPLICATIONS

This application claims priority to U.S. Provisional Patent Application Ser. No. 63/419,863, entitled "PLANTS AND SEEDS OF *BRASSICA CARINATA* HYBRID VARIETY NUJET 400", which was filed on Oct. 27, 2022, the contents of which are incorporated herein by reference.

FIELD OF THE INVENTION

The present invention relates generally to the field of *Brassica carinata* breeding and, more specifically, to the development of a new *Brassica carinata* hybrid variety Nujet 400, a sample of seed of which has been deposited with the American Type Culture Collection (ATCC) under Accession number PTA-127252.

BACKGROUND

*Brassica carinata* is a member of the Brassicaceae (formerly Cruciferae) family, commonly known as the mustard family. In Canada, *Brassica carinata* is commonly known as carinata, but is also sometimes referred to as Ethiopian mustard, Abyssinian mustard, Ethiopian kale or Abyssinian kale. In Ethiopia it is named gomenzer (Getinet, et al., 1996).

The genus *Brassica* is a member of the tribe Brassiceae in the mustard family (Brassicaceae; (Warwick, et al., 2009). In addition to *B. carinata*, the *Brassica* genus includes several economically important oilseed crop species: *B. juncea* (L.) Czern. (brown mustard), *B. napus* L. (rape, Argentine canola), *B. nigra* (L.) W. D. J. Koch (black mustard), and *B. rapa* L. (field mustard, Polish canola). The genus *Brassica* also includes *B. oleracea* L. food crops, including cabbage, broccoli, cauliflower, brussels sprouts, kohlrabi and kale.

The six *Brassica* species are closely related genetically, as described in the Triangle of U (Nagaharu, 1935). *Brassica carinata* is an amphidiploid (BBCC, 2n=34) thought to be derived from interspecific hybridization of the diploid species *B. nigra* L. (BB, 2n=16) and *B. oleracea* L. (CC, 2n=18; (Prakash, et al., 2011). The native range of *Brassica carinata* comprises the central highland region of Ethiopia. All the naturally occurring carinata in these regions is cultivated; there do not appear to be wild populations.

*Brassica carinata* is an herbaceous annual with a determinate growth habit (Zanetti, et al., 2013). The plants were originally cultivated in their home range primarily as a source of leaves used as an edible and nutritious vegetable (Neugart, et al., 2017). Carinata can be grown as a cover crop to reduce soil erosion and herbicide use, while promoting water conservation (Alcantara, et al., 2011) or can be plowed into the soil for use as a green manure soil amendment and bio-fumigant (Lazzeri, et al., 2009; Pane, et al., 2013). Carinata also has utility in phytoremediation of heavy metal-contaminated topsoil (Mourato, et al., 2015). As abundant producers of vegetative biomass, cropping of carinata's above-ground biomass has been suggested as a renewable source of feedstock for conversion to energy, particularly where cultivated in southern Europe (Gasol, et al., 2007).

*Brassica carinata* can be grown in subtropical regions as winter cover crop in rotations with summer crops such as beans, cotton, and peanuts, where the usual practice had been to follow with winter fallow. This is made possible by the unique ability for established carinata to survive and recover after hard frosts (Seepaul, et al., 2015). Benefits of carinata's use as a winter cover crop in this environment include the ability to conserve winter moisture and nutrients in the soil, mitigate leaching of nitrogen, phosphates and other residual nutrients into local waterways, as well as providing a means to increase soil organic carbon (Newman, et al., 2010 (revised)). *Brassica carinata*'s greater tolerance to early season frost, ability to better cope with higher heat and lower moisture during flowering and seed set, as well as resistance to lodging, allows it to better withstand early and late season weather extremes (Seepaul, et al., 2015), making it overall a more reliable oilseed cropping option for producers in semi-arid regions.

*Brassica* crops have long been shown to be beneficial when grown in rotations with cereals such as wheat, an important food crop amenable to production in semiarid regions by virtue of its shorter growing season and tolerance to climate extremes. Rotations with oilseed as well as forage *Brassica* species have consistently demonstrated a beneficial effect on yield of the ensuing cereal crop, due to their effects on improving soil structure and moisture conservation and to its ability to provide a break to the cycle of diseases that affect cereal performance (Angus, et al., 2011). Its ability to break cereal disease cycles stems from *Brassica*'s lack of susceptibility to many cereal diseases, but may also derive from their ability to actively discourage persistence of soil pathogens via the biofumigant activity of root exudates and residues (Kirkegaard and Sarwar, 1998). In the southern hemisphere, the crop can be sown in late autumn or early winter into moist soil. In higher rainfall zones, it can be sown as late as early spring.

In terms of economic value, *Brassica carinata*'s greatest potential as a crop resides in its prolific yields of oil and protein rich seed. In southern Europe, carinata seed oil has been investigated for its potential as a feedstock for biofuel and as a bio-industrial feedstock with applications in production of lubricants, paints, cosmetics, plastics (Cardone, et al., 2002; Cardone, et al., 2003; Bouaid, et al., 2005; Gasol, et al., 2007; Gasol, et al., 2009). In North America, where varieties have been adapted to grow in regions as diverse as the semi-arid southern Canadian prairies and adjacent US northern tier states as well as the Southeast US gulf states, carinata has been shown to be a suitable renewable feedstock crop for biofuel production (Gesch, et al., 2015; Seepaul, et al., 2015), and oil extracted from *B. carinata* seed has been used to produce green bio-diesel and bio-jet fuel (Drenth, et al., 2015). In October 2012, experimental aviation flights by the National Research Council of Canada using the world's first 100% bio-jet fuel were successful ("ReadiJet 100% biofuels flight—one of 2012's 25 most important scientific events", Popular Science Magazine, 2012(12).

Carinata varieties have been developed that are optimized for production of oil feedstock for diverse bio-industrial uses such as manufacturing of bio-plastics (Impallomeni, et al., 2011; Newson, et al., 2014), lubricants (Zanetti, et al., 2009) and specialty fatty acids such as 5,13-docosadienoic acid, 5-eicosenoic acid (Jadhav, et al., 2005), eicosapentaenoic acid (Cheng, et al., 2010) and nervonic acid (Taylor, et al., 2010). In some cases, modification of the seed oil profile has involved the use of transgenic technologies to introduce specific genes encoding enzymes of the fatty acid biosynthesis pathways or constructs to knock down expression of endogenous pathway genes (reviewed in Taylor, et al., 2010).

As well as its high oil content, carinata seed has high protein and low fibre content (Xin and Yu, 2014), making the meal that is produced as a by-product of the oil extraction process a potential source of high quality protein for use in animal feed applications. The native seed also has a high content of glucosinolate (GSL), a class of sulfur containing compounds which, when present at high levels in meal, can reduce feed palatability and adversely affect animal health. There have been efforts to reduce GSL levels through use of interspecific crossing with low GSL varieties of other Brassicaceae species (Getinet, et al., 1997; Marquez-Lema, et al., 2008). More recently, it has been demonstrated that the optimized processing of the meal during the oil extraction process can remove most of the glucosinolate, rendering the meal suitable for a number of animal feed applications (U.S. Publication No. 2018/004226). Carinata meal is currently approved as a supplement for cattle feed in Canada, US and Europe.

*Brassica carinata* has been adapted to meet the demands of emerging markets for carinata seed and carinata products. To provide opportunity to expand its production base, there continues to be a great need in the art for new carinata varieties and lines with improved traits, including increased grain and oil yields per acre, increased seed oil content and optimized oil composition, as well as varieties with improved agronomic traits such as increased tolerances to biotic and abiotic stresses, reduced time to maturity and improved harvestability.

SUMMARY OF THE INVENTION

In one aspect of the invention, a new *Brassica carinata* hybrid variety Nujet 400 is provided. Nujet 400 may be grown as a non-food winter cover crop between primary crops. Nujet 400 provides the benefits of a typical cover crop (such as improved soil health) with increased yield potential in a lower nitrogen input, winter environment as tested in Argentina, Uruguay, and the Southern United States.

In other aspects, the invention also provides a seed, plant, plant part or cell of *Brassica carinata* variety Nujet 400, for which a representative sample of seed has been deposited under ATCC Accession Number PTA-127252. The invention also provides a method of producing a commercial crop, the method comprising planting seed of *Brassica carinata* variety Nujet 400, representative seed of said variety having been deposited under ATCC accession number PTA-127252, and growing the commercial crop.

In other aspects, the invention is also directed to a cell, seed, plant, or plant part of a *Brassica carinata* variety produced by crossing *Brassica carinata* variety Nujet 400 with other *Brassica carinata* varieties.

In another aspect, the invention is directed to a *Brassica carinata* seed produced by crossing *Brassica carinata* plants and harvesting the resulting *Brassica carinata* seed, wherein at least one *Brassica carinata* plant is the plant of *Brassica carinata* variety Nujet 400. In another aspect, the invention is directed to a method of producing a *Brassica carinata* variety derived from *Brassica carinata* variety Nujet 400, the method comprising (a) crossing *Brassica carinata* variety Nujet 400 plant with a different *Brassica carinata* plant having a desired trait to produce F1 hybrid seed; and (b) growing the resultant F1 hybrid seed and selecting one or more F1 hybrid progeny plants having the desired trait and at least a portion of the genetic make up of *Brassica carinata* variety Nujet 400, followed by fixing the trait in an inbred background via DH methodology or repeated self-pollination. In another embodiment, the method of producing a *Brassica carinata* variety derived from *Brassica carinata* variety Nujet 400 further comprises the steps of (a) self-pollinating the selected F1 hybrid progeny plants to produce further progeny seed; (b) growing the further progeny seed and selecting further progeny plants that have the desired trait and at least a portion of the genetic make up of *Brassica carinata* variety Nujet 400; and (c) repeating steps (a) and (b) on the selected further progeny plants to a maximum of 10 generations to produce a progeny *Brassica carinata* plant derived from *Brassica carinata* variety Nujet 400, wherein the progeny *Brassica carinata* plant comprises the desired trait and at least a portion of the genetic make up of *Brassica carinata* variety Nujet 400. The invention is also directed to a cell, seed, plant, or plant part of a *Brassica carinata* variety derived from *Brassica carinata* variety Nujet 400 using the above-described methods.

In another aspect, the invention provides methods for producing doubled haploid (DH) varieties from $F_1$ *Brassica carinata* plants produced by crossing *Brassica carinata* Nujet 400 variety with other *Brassica carinata* varieties (derived from $F_1$ Nujet 400 hybrid x other *Brassica carinata* varieties) or from $F_2$ seed from self-pollination of Nujet 400, as well as a cell, seed, plant, or plant part produced by such DH varieties and any progeny of these.

In another aspect, the invention provides methods for producing a *Brassica carinata* plant by outcrossing (aka interspecific crossing) *Brassica carinata* variety Nujet 400 with other Brassicaceae species followed by backcrossing with *Brassica carinata* variety Nujet 400, as well as producing DH varieties from the interspecific crosses. In some embodiments, the other Brassicaceae species may be any species of the family Brassicaceae including but not limited to *Brassica alba, Brassica hirta, Brassica juncea, Brassica napus, Brassica nigra, Brassica oleracea, Brassica rapa, Sinapus alba*, and *Camelina sativa*. In some embodiments, the progeny DH varieties retain the "essential morphological or physiological characteristics" of *Brassica carinata* variety Nujet 400 as described herein, when grown in the same location under the same environmental conditions. In some embodiments, the "essential morphological or physiological characteristics" of *Brassica carinata* variety Nujet 400 are the physiological and/or morphological characteristics set forth in one or more of Tables 1, 2, 3, 4, 5, 6, 7, and 8 as determined at the 5% significance level.

In another aspect, the invention provides for the use of *Brassica carinata* variety Nujet 400 as a background for chemical and/or radiation induced mutagenesis, for targeted gene editing, for modulation of traits via RNA interference or antisense RNA expression, or for introduction of traits via genetic transformation.

In another aspect, the invention provides a method to produce a commercial crop of plants of *Brassica carinata* variety Nujet 400, as well any progeny plants derived from *Brassica carinata* variety Nujet 400. The invention also provides a method of producing a commercial plant product comprising growing the plant of *Brassica carinata* variety Nujet 400, or any progeny plants derived from *Brassica carinata* variety Nujet 400, to produce a commercial crop and producing the commercial plant product from the commercial crop.

In other aspects, the invention relates to the use of *Brassica carinata* variety Nujet 400 to produce a commercial product, such as oil, meal, protein isolate, biofumigant, or crushed non-viable seed. The invention also provides for commercial products produced from *Brassica carinata* variety Nujet 400, as well any progeny plants derived from

*Brassica carinata* variety Nujet 400, including but not limited to oil, meal, protein isolate, biofumigant, or crushed non-viable seed.

The invention provides for, without limitation, the following numbered embodiments:

1. *Brassica carinata* variety Nujet 400, representative seed of the variety having been deposited under ATCC accession number PTA-127252.
2. A seed, plant, plant part or cell of *Brassica carinata* variety Nujet 400, representative seed of the variety having been deposited under ATCC accession number PTA-127252.
3. A *Brassica carinata* seed produced by crossing a plant of *Brassica carinata* variety Nujet 400 with a different *Brassica carinata* plant to produce F1 hybrid seed, representative seed of variety Nujet 400 having been deposited under ATCC accession number PTA-127252, and recovering the F1 hybrid seed.
4. A method of producing a *Brassica carinata* variety derived from *Brassica carinata* variety Nujet 400, the method comprising
   (a) crossing a plant of *Brassica carinata* variety Nujet 400 with a different *Brassica carinata* plant having a desired trait to produce F1 hybrid seed; and
   (b) growing the resultant F1 hybrid seed and selecting one or more F1 hybrid plants having the desired trait.
5. The method of embodiment 4, further comprising the steps of
   (a) self-pollinating the F1 hybrid plants to produce further progeny seed;
   (b) growing the further progeny seed and selecting further progeny plants that have the desired trait; and
   (c) repeating steps (a) and (b) on the selected further progeny plants to a maximum of 10 generations to produce a *Brassica carinata* plant derived from *Brassica carinata* variety Nujet 400, wherein the *Brassica carinata* plant comprises the desired trait and all the physiological and morphological characteristics of *Brassica carinata* variety Nujet 400 other than the desired trait.
6. A cell, seed, plant, or plant part of the *Brassica carinata* variety produced by the method of any one of embodiments 4 to 5, wherein the *Brassica carinata* plant has the same physiological and/or morphological characteristics set forth in one or more of Tables 1, 2, 3, 4, 5, 6, 7, and 8, as determined at the 5% significance level, when grown in the same location under the same environmental conditions as variety Nujet 400 as a plant of variety Nujet 400.
7. A method of producing a commercial plant product, the method comprising growing the plant of embodiment 2 to produce a commercial crop and producing the commercial plant product from the commercial crop.
8. The method of embodiment 7, wherein the commercial plant product comprises oil, meal, protein isolate, or biofumigant.
9. A method of producing a commercial plant product, the method comprising growing the plant of embodiment 6 to produce a commercial crop and producing the commercial plant product from the commercial crop.
10. The method of embodiment 9, wherein the commercial plant product comprises oil, meal, protein isolate, or biofumigant.
11. A commercial crop produced from the *Brassica carinata* plant of embodiments 2 or 6.
12. A product produced from the *Brassica carinata* plant of variety Nujet 400, wherein said product optionally comprises at least one cell of said *Brassica carinata* plant of variety Nujet 400.
13. A product produced from the *Brassica carinata* plant of embodiments 2 or 6, wherein the product comprises oil, meal, protein isolate or biofumigant.
14. The plant part of embodiment 2, wherein the plant part is an ovule, a leaf, pollen, a seed, an embryo, a root, a root tip, a pod, a flower, a stalk, a cell, or a protoplast.
15. The plant part of embodiment 14, wherein the plant part is pollen.
16. The plant part of embodiment 14, wherein the plant part is an ovule.
17. A *Brassica carinata* plant or plant part having essentially all the physiological and morphological characteristics of the plant of embodiment 2 when grown in the same location under the same environmental conditions.
18. A *Brassica carinata* plant or plant part having the physiological and/or morphological characteristics set forth in one or more of Tables 1, 2, 3, 4, 5, 6, 7, and 8, as determined at the 5% significance level, when grown in the same location under the same environmental conditions as variety Nujet 400.
19. A method for producing *Brassica carinata* seed comprising crossing *Brassica carinata* plants and harvesting the resulting *Brassica carinata* seed, wherein at least one *Brassica carinata* plant is the plant of embodiment 2.
20. A method for producing a Double Haploid variety comprising:
   (a) isolating a flower bud of the F1 plant derived from a cross involving Nujet 400;
   (b) dissecting out a haploid microspore;
   (c) placing the haploid microspore in culture;
   (d) inducing the microspore to differentiate into an embryo and subsequently into a plantlet;
   (e) identifying whether the plantlet contains a diploid chromosome number, wherein the diploid chromosome number occurred through chromosome doubling; and
   (f) continuing to grow the plantlet if it contains a diploid chromosome number.
21. The method of embodiment 20 further comprising inducing chromosome doubling by chemical or physical means.
22. A cell, plant, plant part, or seed of a Doubled Haploid variety produced by the method of embodiment 20 or 21.
23. A method of producing a *Brassica carinata* variety from the plant of embodiment 2, wherein the *Brassica carinata* variety comprises a desired trait, the method comprising introducing a nucleic acid construct conferring the desired trait into a *Brassica carinata* plant of variety Nujet 400.
24. The method of embodiment 23, wherein the nucleic acid construct is introduced using polyethylene glycol (PEG) mediated nucleic acid uptake, electroporation, ballistic infiltration using nucleic acid coated microprojectiles (gene gun), an *Agrobacterium* infiltration-based vector, or a plant virus based vector.
25. The method of embodiment 23 or 24, wherein the nucleic acid construct comprises a transgene, an RNAi construct, or an antisense RNA construct.
26. The method of any one of embodiments 23 to 25, wherein the *Brassica carinata* variety comprises the desired trait and the physiological and/or morphological characteristics set forth in one or more of Tables 1, 2, 3, 4, 5, 6, 7, and 8, as determined at the 5% significance level, when grown in the same location under the same environmental conditions as variety Nujet 400.

27. A method of producing a *Brassica carinata* variety from the plant of embodiment 2, wherein the *Brassica carinata* variety comprises a desired trait, the method comprising the steps of:
   (a) crossing a plant of variety Nujet 400 with another *Brassica carinata* variety comprising the desired trait;
   (b) growing the resultant F1 hybrid seed and selecting one or more progeny plants that have the desired trait;
   (c) self-pollinating the progeny plants that have the desired trait to produce further progeny seed; and
   (d) growing the further progeny seed and selecting further progeny plants that have the desired trait,
   wherein the *Brassica carinata* variety derived from the plant of embodiment 2 comprises at least a portion of the genetic makeup of *Brassica carinata* variety Nujet 400.
28. The method of embodiment 27, wherein steps (c) and (d) are repeated until the *Brassica carinata* variety from variety Nujet 400 has the desired trait the physiological and/or morphological characteristics set forth in one or more of Tables 1, 2, 3, 4, 5, 6, 7, and 8, as determined at the 5% significance level, when grown in the same location under the same environmental conditions as variety Nujet 400.
29. A method of producing a *Brassica carinata* variety produced from the plant of embodiment 2, wherein the *Brassica carinata* variety comprises a new trait and the method comprises exposing seedlings or microspores to a mutagenic agent and allowing the surviving fraction to develop into mature plants.
30. The method of embodiment 29, wherein the mutagenic agent is ethyl methanesulfonate, N-ethyl-N-nitrosourea, or x-ray, gamma or ultraviolet radiation.
31. A method of producing a *Brassica carinata* variety derived from the plant of embodiment 2, wherein the *Brassica carinata* variety comprises a desired trait, the method comprising:
   (a) crossing a plant of variety Nujet 400 with a plant of another species of the family Brassicaceae comprising the desired trait;
   (b) producing F1 plants using embryo rescue techniques to recover viable F1 plants or growing F1 seeds;
   (c) self-pollinating the F1 plants that have the desired trait and carinata character;
   (d) producing F2 plants using embryo rescue techniques to recover viable F2 plants or growing F2 seeds;
   (e) self-pollinating the F2 plants that have the desired trait and carinata character;
   (f) producing F3 plants using embryo rescue techniques to recover viable F2 plants or growing F3 seeds;
   (g) self-pollinating the progeny plants that have the desired trait and carinata character to produce further progeny plants; and
   (h) selecting further progeny plants with the desired trait and carinata character to produce the carinata variety,
   wherein the *Brassica carinata* variety derived from the plant of embodiment 2 comprises at least a portion of the genetic makeup of *Brassica carinata* variety Nujet 400.
32. The method of embodiment 31, wherein steps (g) and (h) are repeated until the *Brassica carinata* variety produced from variety Nujet 400 has the desired trait and the physiological and/or morphological characteristics set forth in one or more of Tables 1, 2, 3, 4, 5, 6, 7, and 8, as determined at the 5% significance level, when grown in the same location under the same environmental conditions as variety Nujet 400.
33. The method any one of embodiments 23 to 32, wherein the desired trait is selected from the group consisting of male sterility and/or fertility restoration, disease resistance, fungal resistance, pest resistance, herbicide tolerance, abiotic stress tolerance, and altered metabolism.
34. The method of embodiment 33, wherein the desired trait is herbicide tolerance and the herbicide is selected from, but not limited to, the group consisting of glyphosate, glufosinate, imidazolinones, and auxin analogues such as 2,4-D and dicamba.
35. A plant, plant part, cell, or seed of a progeny *Brassica carinata* variety produced by the method of any one of embodiments 23 to.
36. A method of producing a commercial crop, the method comprising planting seed of *Brassica carinata* variety Nujet 400, representative seed of said variety having been deposited under ATCC accession number PTA-127252, and growing the commercial crop.
37. Crushed, non-viable seed of *Brassica carinata* variety Nujet 400, wherein a representative sample of the seed has been deposited under ATCC Accession number PTA-127252.
38. A cell of a seed, plant or plant part of *Brassica carinata* variety designated Nujet 400, wherein a representative sample of the seed has been deposited under ATCC Accession number PTA-127252.
39. A protoplast of the cell of embodiment 38.
40. A cell of a *Brassica carinata* plant or plant part having the physiological and/or morphological characteristics set forth in one or more of Tables 1, 2, 3, 4, 5, 6, 7, and 8, as determined at the 5% significance level, when grown in the same location under the same environmental conditions as variety Nujet 400.
41. The cell of embodiment 40, wherein the plant part is an ovule, a leaf, pollen, a seed, an embryo a root, a root tip, a pod, a flower, or a stalk.
42. A tissue culture of protoplasts or regenerable cells of the cell of embodiment 40 or 41.
43. The tissue culture according to embodiment 42, wherein the protoplasts or regenerable cells are produced from a tissue selected from the group consisting of leaves, pollen, embryos, roots, root tips, pods, flowers, ovules, and stalks.
44. A *Brassica carinata* plant regenerated from the tissue culture of embodiment 43, wherein the plant has the physiological and/or morphological characteristics set forth in one or more of Tables 1, 2, 3, 4, 5, 6, 7, and 8, as determined at the 5% significance level, when grown in the same location under the same environmental conditions as variety Nujet 400.
45. A cell of a *Brassica carinata* plant regenerated from the tissue culture of embodiment 43, wherein the plant has the physiological and/or morphological characteristics set forth in one or more of Tables 1, 2, 3, 4, 5, 6, 7, and 8, as determined at the 5% significance level, when grown in the same location under the same environmental conditions as variety Nujet 400.

46. Use of a plant of *Brassica carinata* variety Nujet 400 to produce seed, wherein the seed is produced by self-crossing or open pollination.
47. Use of a plant of *Brassica carinata* variety Nujet 400 to produce an F1 hybrid *Brassica carinata* seed, wherein the plant of *Brassica carinata* variety Nujet 400 is either a female parent or a male parent in a cross-fertilization.
48. A cell of an F1 hybrid plant grown from the F1 hybrid seed produced by the use of embodiment 46.
49. A cell of an F1 hybrid plant grown from F1 hybrid seed produced by a method comprising crossing a plant of *Brassica carinata* variety Nujet 400 with a different *Brassica carinata* plant and harvesting the resultant F1 hybrid carinata seed.
50. Use of a plant of *Brassica carinata* variety Nujet 400 to produce a Double Haploid variety.
51. Use of embodiment 50, wherein the Double Haploid variety is produced by a method comprising chromosome doubling introduced by chemical or physical means.
52. A cell of a Double Haploid (DH) variety produced from *Brassica carinata* variety Nujet 400.
53. Use of a plant of *Brassica carinata* variety Nujet 400 to produce a *Brassica carinata* variety comprising a desired trait.
54. Use of a plant of *Brassica carinata* variety Nujet 400 to produce a *Brassica carinata* variety comprising a desired trait, wherein the desired trait is conferred by a nucleic acid construct.
55. The use of embodiment 54, wherein the nucleic acid construct is introduced using polyethylene glycol (PEG) mediated uptake, electroporation, ballistic infiltration using nucleic acid-coated microprojectiles (gene gun), an *Agrobacterium* infiltration-based vector, or a plant virus-based vector.
56. The use of embodiment 54 or 55, wherein the nucleic acid construct comprises a transgene, an RNAi construct, or an antisense RNA construct.
57. Use of a plant of *Brassica carinata* variety Nujet 400 to produce a *Brassica carinata* variety comprising a desired trait, wherein the desired trait is introduced by exposing seedlings or microspores to a mutagenic agent.
58. The use of embodiment 57, wherein the mutagenic agent is ethyl methanesulfonate, N-ethyl-N-nitrosourea, or x-ray, gamma or ultraviolet radiation.
59. Use of a plant of *Brassica carinata* variety Nujet 400 to produce a *Brassica carinata* variety comprising a desired trait, wherein the desired trait is introduced by crossing a plant of variety Nujet 400 with a plant of another Brassicaceae species comprising the desired trait.
60. The use of embodiment 59, wherein the *Brassica carinata* variety produced from variety Nujet 400 has the desired trait and the physiological and/or morphological characteristics set forth in one or more of Tables 1, 2, 3, 4, 5, 6, 7, and 8, as determined at the 5% significance level, when grown in the same location under the same environmental conditions as variety Nujet 400.
61. The use of any one of embodiments 53 to 60, wherein the desired trait is selected from the group consisting of male sterility, disease resistance, fungal resistance, pest resistance, herbicide tolerance, abiotic stress tolerance, and altered metabolism.
62. The use of embodiment 61 wherein the desired trait is herbicide tolerance and the herbicide selected from, but not limited to, the group consisting of glyphosate, glufosinate, imidazolinones, and auxin analogues such as 2,4-D and dicamba.
63. A cell of a plant of a *Brassica carinata* variety produced from variety Nujet 400, wherein the *Brassica carinata* variety comprises a desired trait, and wherein the *Brassica carinata* variety was produced by a method comprising introducing a nucleic acid construct conferring the desired trait into a plant, plant part, or cell of variety Nujet 400.
64. The cell of embodiment 63, wherein the nucleic acid construct is introduced using polyethylene glycol (PEG) mediated uptake, electroporation, ballistic infiltration using nucleic acid coated microprojectiles (gene gun), an *Agrobacterium* infiltration-based vector, or a plant virus-based vector.
65. The cell of embodiment 63 or 64, wherein the nucleic acid construct comprises a transgene, an RNAi construct, or an antisense RNA construct.
66. The cell of any one of embodiments 63 to 65, wherein the *Brassica carinata* variety produced from variety Nujet 400 comprises the desired trait and the physiological and/or morphological characteristics set forth in one or more of Tables 1, 2, 3, 4, 5, 6, 7, and 8, as determined at the 5% significance level, when grown in the same location under the same environmental conditions as variety Nujet 400.
67. A cell of a plant of a *Brassica carinata* variety produced from variety Nujet 400, wherein the *Brassica carinata* variety comprises a desired trait, and wherein the *Brassica carinata* variety was produced by a method comprising the steps of:
    (a) crossing a plant of variety Nujet 400 with a plant of another *Brassica carinata* variety comprising the desired trait;
    (b) growing the resultant F1 hybrid seed and selecting one or more progeny plants that have the desired trait;
    (c) self-pollinating the progeny plants that have the desired trait to produce further progeny plants;
    (d) growing the resultant further progeny plants and selecting further progeny plants that have the desired trait and at least a portion of the genetic make up of *Brassica carinata* variety Nujet 400.
68. The cell of embodiment 67, wherein steps (c) and (d) are repeated until the *Brassica carinata* variety produced from variety Nujet 400 has the desired trait and the physiological and/or morphological characteristics set forth in one or more of Tables 1, 2, 3, 4, 5, 6, 7, and 8, as determined at the 5% significance level, when grown in the same location under the same environmental conditions as variety Nujet 400.
69. A cell of a plant of a *Brassica carinata* variety produced from variety Nujet 400, wherein the *Brassica carinata* variety comprises a new trait and is produced by a method comprising exposing seedlings or microspores to a mutagenic agent and allowing the surviving fraction to develop into mature plants.
70. The cell of embodiment 69, wherein the mutagenic agent is ethyl methanesulfonate, N-ethyl-N-nitrosourea, or x-ray, gamma or ultraviolet radiation.

71. A cell of a plant of a *Brassica carinata* variety comprising a desired trait, wherein the *Brassica carinata* variety is produced by a method comprising:
   (a) crossing a plant of variety Nujet 400 with a plant of another Brassicaceae species comprising the desired trait;
   (b) producing F1 plants using embryo rescue techniques to recover viable F1 plants from the cross or growing F1 seeds;
   (c) self-pollinating the F1 plants that have the desired trait and carinata character;
   (d) producing F2 plants using embryo rescue techniques to recover viable F1 plants from the cross or growing F2 seeds;
   (e) self-pollinating the F2 plants that have the desired trait and carinata character;
   (f) producing progeny plants using embryo rescue techniques to recover viable F3 plants or growing F3 seeds;
   (g) self-pollinating the progeny plants that have the desired trait and carinata character to produce further progeny plants; and
   (h) selecting the progeny plants with the desired trait and carinata character.
72. The cell of embodiment 71, wherein steps (g) and (h) are repeated until the *Brassica carinata* variety produced from variety Nujet 400 has the desired trait and the physiological and/or morphological characteristics set forth in one or more of Tables 1, 2, 3, 4, 5, 6, 7, and 8, as determined at the 5% significance level, when grown in the same location under the same environmental conditions as variety Nujet 400.
73. The cell of any one of embodiments 63 to 72, wherein the desired trait is selected from the group consisting of male sterility, disease resistance, fungal resistance, pest resistance, herbicide tolerance, abiotic stress tolerance, and altered metabolism.
74. The cell of embodiment 73, wherein the desired trait is herbicide tolerance and the herbicide is selected from, but not limited to, the group consisting of glyphosate, glufosinate, imidazolinones, and auxin analogues such as 2,4-D and dicamba.
75. Use of a plant of *Brassica carinata* variety Nujet 400 to produce a commercial crop.
76. Use of a plant of *Brassica carinata* variety Nujet 400 to produce a commercial plant product.
77. The use of embodiment 76, wherein the commercial plant product comprises oil, meal, protein isolate, or biofumigant.
78. A method for producing a group of cultivated plants of *Brassica carinata* variety Nujet 400 in a field, wherein harmful microorganisms are controlled by the application of a composition comprising one or more microbiocidal ingredient.
79. The method of embodiment 78, wherein the one or more microbiocidal ingredient is selected from the group comprising iprodione, prothiaconazole vinclozolin, boscalid, carbathiin, thiram, difenoconazole, metalaxyl, sedaxane, fludioxonil, penflufen, trifloxystrobin, and sedaxane.
80. The method of embodiment 79, wherein the composition comprising one or more microbiocidal ingredient is applied as a seed treatment or seed coating.
81. A method for producing a group of cultivated plants of *Brassica carinata* variety Nujet 400 in a field, wherein insect pests are controlled by the application of a composition comprising one or more insecticidal ingredient.
82. The method of embodiment 81, wherein the insecticidal ingredient is applied as a seed treatment or foliar treatment.
83. A method for cleaning seed of *Brassica carinata* variety Nujet 400, or seed from a plant produced from *Brassica carinata* variety Nujet 400, to remove foreign material from the surface of the seed.
84. A method for cleaning seed of *Brassica carinata* variety Nujet 400, or seed from a plant produced from *Brassica carinata* variety Nujet 400, to remove any debris or low quality, infested, or infected seeds, or seeds of different species.

Definitions

In the following description and tables, many terms are used. To aid in a clear and consistent understanding of the specification, the following definitions and evaluation criteria are provided.

Abiotic stress is defined as the negative impact of non-living factors on the living organisms in a specific environment. Examples of abiotic stress include, but are not limited to, drought, water-logging or flooding, extreme temperatures, extreme salinity, and mineral toxicity.

Agronomic practice refers to any of a set of cultivation practices or techniques that attempt to maximize the health and productivity of a crop. The agronomic practices used are an important factor in interpreting results from field studies of various kinds.

Allele refers to one or more alternative forms of a gene locus that relate to one trait. Diploid organisms, i.e., organisms with two sets of chromosomes, have one copy of each gene (and therefore, one allele) on each chromosome. If both the alleles are the same, they are homozygous. If the alleles are different, they are heterozygous.

Alternaria resistance is typically rated on a scale from 0-5; 0=no symptoms were observed, 1=indicates infection of pods only, 2=disease prevalence on 25% of upper plant, 3=50% prevalence, 4=75% prevalence, and 5=disease symptoms are seen throughout entire plant and considered severe.

Average refers to the arithmetic mean. "Substantially equivalent" or "statistically equivalent" refers to a characteristic that, when compared, does not show a statistically significant difference from the mean. In contrast, "statistically different" or "statistical significance" refers to a characteristic that, when compared, shows statistically significant differences from means of the same characteristic of another group or groups. Most often, statistical significance of differences is measured at levels of $P<0.05$ using standard tests to compare Least Square Means, such as Tukey's HSD or Student's t-test.

Backcrossing means a traditional breeding technique used to introduce a trait to a plant line or variant from a donor plant to a recurrent plant. An initial cross is made between the donor and recurrent parent plants to produce progeny plants. Progeny plants having the desired trait are then crossed to the recurrent parent. This process of backcrossing is repeated for several breeding cycles until the progeny plants are indistinguishable from the recurrent parent, except for the trait from the donor parent.

Breeding line (or Plant line) refers to a unique, reproducible carinata type, and is distinguishable from other carinata types based on its genotype and phenotype. Most often, a breeding line refers to a type that is mostly or completely homozygous, such as a DH line or a highly inbred line (five or more generations inbred).

Carinata refers to seeds or plants of the species *Brassica carinata* containing both the B genome from *Brassica nigra* and the C genome from *Brassica oleracea* (Nagahuru, 1935). The terms "*Brassica carinata* variety Nujet 400", "carinata variety Nujet 400", "variety Nujet 400", and "Nujet 400" are used interchangeably herein and refer to a plant of *Brassica carinata* variety Nujet 400, representative seed of which having been deposited under ATCC Accession number PTA-127252.

Check variety (or Check line) are carinata genotypes considered to be the standard for overall performance, or for a specified trait, in a given growing region. Often, the current commercial varieties are used as check lines for the regions in which they are grown, and this is the standard against which new potential varieties are tested. Examples of useful commercial check varieties include, but are not limited to, *Brassica carinata* varieties Avanza 641 and Nuola 300 (a hybrid canola variety grown in the same environments). Avanza 641 is described in detail in WO2017/181276A1, where it is referred to as "AGRO44-312D-HP11".

Days to Flowering (initiation of flowering) refers to the number of days from planting until 50% of the plants in a planted area have at least one open flower.

Depth of canopy, measured in cm, is the distance from the first incidence of pods on a plant (average within a plot) to the top of the pod canopy.

Diploid refers to cell or a plant with two sets of chromosomes. One set comes from each parent.

Double Haploid, Doubled Haploid, Doubled Haploidy (DH) refers to a haploid cell or plant that has undergone a doubling of its chromosomes to produce a functional diploid.

Duration of flowering is the number of days between the initiation of flowering and end of flowering.

Early (season) vigour is a rating, usually on a scale of 1 to 7, that reflects how a variety develops in its early stages (about 4 weeks after seed) in terms of putting on leaf area and competing with weeds. Typically, experimental varieties or lines are compared with a check variety or line. A new variety with slightly more leaf cover and advanced development would be rated one point higher, and significantly more leaf cover would be rated two points higher. Conversely, a new variety with slightly less leaf cover would be rated one point lower, and significantly less two points lower.

End of flowering is the number of days from planting to when approximately 90% of flowers have lost their petals.

Erucic Acid content is the weight percentage (wt %) of fatty acids in the form of C22:1 among all major fatty acid types found in carinata. Most often, this is estimated by Near Infrared Spectroscopy (NIR) of mature seeds at less than 6% moisture. The NIR is calibrated using a large array of samples whose fatty acid profile is determined by American Oil Chemists Society (AOCS) Official Method Cel-66 Fatty Acid Composition by Gas Chromatography. This is one of the official methods recommended by the Western Canada Canola/Rapeseed Recommending Committee (WCC/RCC).

Extent of branching refers to the number of pod-bearing secondary branches (racemes) off the main stem. This is often estimated using an average of at least eight plants per breeding line.

Embryo Rescue techniques refers to in vitro techniques whose purpose is to promote the development of an immature or weak embryo into a viable plant. This methodology is commonly used to rescue viable embryos from crosses between different but closely related species, i.e., interspecific crosses.

Fatty acid content means the typical percentages by weight of fatty acids present in the endogenously formed oil of the mature whole dried seeds, as determined by Near Infrared Spectroscopy at less than 6% seed moisture. The NIR is calibrated using a large array of samples whose fatty acid profile is determined by American Oil Chemists Society (AOCS) Official Method Cel-66 Fatty Acid Composition by Gas Chromatography. This is one of the official methods recommended by the Western Canada Canola/Rapeseed Recommending Committee (WCC/RCC). Aside from erucic acid (C22:1), the most significantly occurring fatty acids in carinata are oleic acid (C18:1), linoleic acid (C18:2), linolenic acid (C18:3), and eicosenoic acid (C20:1).

Flower Petal Colouration means the colouration of open exposed petals on the first day that flowering is observed. In carinata, varieties are most often categorized as either W=White or Y=Yellow. Occasionally, for varieties with a very light yellow colour, a third category will be employed: PY=Pale Yellow.

Frost tolerance means the ability of young plants to withstand frosts in areas where carinata is grown during the winter season. These frosts are most likely to occur from the five-leaf to early bolting plant development stages, depending on time of planting. This is typically measured 3-5 days following a hard frost event and rated using a scale of visual percentage of injury (leaf bleaching and death); where "0" is no injury and "10" is 100% plant damage, and each successive number indicates an additional 10% injury to leaf and stem tissue.

Gene silencing means the interruption or suppression of the expression of a gene at the level of transcription or translation.

Genotype refers to the genetics or DNA sequence of individual carinata lines, as opposed to their actual appearance, which is called the phenotype.

Glucosinolate (GSL) content means the total glucosinolate content of mature seed at less than 6% moisture, given in units of μmol/g, as analyzed using Near Infrared Spectroscopy. In carinata, the majority of glucosinolate content is in the form of sinigrin (chemical name: allylglucosinolate or 2-propenylglucosinolate). Most often, the total glucosinolate content of seeds is estimated by Near Infrared Spectroscopy (NIR) of mature seeds at less than 6% moisture. The NIR is calibrated using a large array of samples with known GSL content determined previously by one or more methods known in the art including, but not limited to, gas chromatography of TMS-derivatives, and HPLC of desulfoglucosinolates.

Grain means the seed produced by carinata crops that are intended for processing for oil or feed uses. This is in contrast with parent seed or planting seed, which is intended for growth of another generation of plants.

Growing Degree Days refers to the accumulation of heat units above a base temperature over time and is often strongly correlated with rate of plant development. The daily GDD units are calculated by subtracting the average temperature (° C.) (average of daily maximum and minimum temperature) from the baseline of 5° C. These units accumulate beginning the day after planting.

Growing Environment refers to a particular area (typically grouped by geography) or controlled environment where plants are grown and evaluated. Expression of various characteristics or traits, such as plant height or days to maturity, can be greatly influenced by the environment in which it is grown. This is also commonly known as Genotype×Environment interaction, or G×E.

Haploid refers to a plant, or a cell of a plant, that has only one set of chromosomes. Haploid plants can be produced artificially, and their single set of chromosomes can be doubled to produce a doubled haploid.

Height of first pod, measured in cm, refers to the distance from ground level to the first incidence of pods on a plant (average within a plot).

Herbicide Resistance means the resistance to various herbicides when that herbicide is applied at standard recommended application rates and timing; and is expressed on a scale of 0 to 10; where "0" is no symptoms, and a rating of "10" means entire plant is brown and curled. Each successive number indicates approximately 10% more damage or effect of herbicide on the plant: a rating of "2" indicates several leaves with slight yellowing and curl, "4" is several yellowing or dying leaves and more noticeable curl, "6" is a greater number and severity of yellowing, curling, and dead leaves, and "8" indicates that most leaves are completely yellow or dead.

Hybrid (HYB) variety or F1 hybrid refers to the seeds harvested from crossing two inbred (nearly homozygous) parental lines. This is most often accomplished in carinata through the development of inbred parents using the Ogura pollination control system, where one parent is functionally male sterile (CMS or A-line) and the other restores fertility to the F1 hybrid (Rf or R-line).

Leaf colour means the colour of the leaf blade of lower leaves at the late bolting to early flowering stages (on a plot basis). A categorical scale is most often used, where DG=Dark green; G=Green; LG=Light green; BG=Bluish green.

Leaf glaucosity refers to the presence or absence of a fine whitish powdery coating on the surface of the leaves, and the degree thereof, when present. Numerical scale used to rate this trait: 3=weak, 5=medium, 7=strong.

Leaf Length is the total length of the leaf from attachment of the petiole to the stem, to the tip of the blade, measured in cm, of lower leaves at the late bolting to early flowering stages. It is estimated using an average of measurements from at least 30 plants.

Leaf number of Lobes means the frequency of leaf lobes, when present, of lower leaves at the late bolting to early flowering stages. 3=few, 5=medium, 7=many.

Leaf Width is the width, in cm, of the widest part of the leaf blade of lower leaves at the late bolting to early flowering stages. It is estimated using an average of measurements from at least 30 plants.

Locus refers to a specific location in a chromosome.

Lodging, is the displacement of stems from their vertical and proper placement, observed as extent to which plants of a given variety remain upright; upright plants are easier to harvest with harvesting equipment. In some trials, lodging is measured on a scale of 1-5, where 1=significantly less lodging than check variety; 5=significantly greater lodging than check variety. In other trials, lodging is measured on a scale of 1-7, where 1=plot flat on the ground; 2=most of plot on ground; 3=75% lodged; 4=50% lodged; 5=25% lodged; 6=only slight lodging/stem bending noticed; 7=no lodging.

Maturity may be determined based on Seed Maturity, Physiological Maturity or both. For seed maturity, this is often characterized by the date at which 70% of seeds are hard and have visually changed colour. For physiological maturity, this is often determined as the date when the majority of vegetative parts (stems and pods) appear dry and have visually changed colour.

Near Infrared Spectroscopy (NIR) refers to a non-destructive, spectrometric method commonly used to assess seed quality parameters in grain producing crops. Estimates of total seed oil content and fatty acid profile, as well as total glucosinolate and protein content on a whole seed basis, are examples of parameters for which NIR is commonly employed.

Number of seed-bearing pods is determined by counting the number of pods containing at least one viable seed on the main raceme, as measured in at least eight plants of the same line at full pod set stage.

Oil content means the typical percentage by weight (wt %) of oil present in the mature whole dried seeds, at less than 6% moisture, as determined near infrared (NIR) spectroscopy (AOCS Procedure Am 1-92 Determination of Oil, Moisture and Volatile Matter, and Protein by Near-Infrared Reflectance).

Open-pollinated (OP) variety refers to varieties that are maintained and propagated primarily by means of self-pollination, and for which the next generation will be largely equivalent to the previous.

Pedicel Length is the typical length of the silique stem observed when mature, measured in mm, for 30 pods taken per plot, from pods occurring on mid-third of the main raceme.

Petiole Length is the length of the petiole, measured in cm, from attachment of the petiole to the stem, to the start of the leaf blade, as observed in lower leaves at the late bolting to early flowering stages.

Phenotype refers to the outward appearance or manifestation of given traits of varieties, individual plants, or plant parts (such as leaves or seeds).

Physiological maturity means the number of days from planting to the stage when pods with seed change colour, from green to a dry tan look and when about 70-80% of stems and pods dry-down, corresponding to stages 90 and beyond of the BBCH scale (Meier, et al., 2009).

Plant includes the whole plant, or any plant parts such as plant organs, plant cells, plant protoplasts, plant cell cultures, or plant tissue cultures from which whole plants can be regenerated, plant callus, plant cell clumps, plant transplants, seedlings, plant cells that are intact in plants, plant clones or micropropagations.

Plant height means the overall plant height from ground level to the average of the top of the plant canopy, in cm, taken between mid-flowering and full pod-set stages of plant development.

Plant length is the length of the plant, in cm, measured at maturity. For this trait, it is typically an average 30 or more plants measured individually from the same variety.

Plant part includes, but is not limited to, harvested tissues, fruits, organs, plant cuttings, vegetative propagations, embryos, pollen, ovules, flowers, leaves, fruits, fruit flesh, seeds, clonally propagated plants, roots, stems, stalks, root tips, grafts, parts of any of these and the like, or derivatives thereof, preferably having the same genetic makeup (or very similar genetic make up) as the plant from which it is obtained. Plant part also includes any developmental stage, such as seedlings, cutting prior or after rooting, mature and/or immature plants, or mature and/or immature leaves.

Ploidy refers to the number of sets of chromosomes exhibited by the line, for example, diploid (two sets) or tetraploid (four sets).

Plot refers to a group of carinata plants, grown in one or multiple rows of varying lengths, which is often used as the basic unit of measurement for a number of traits. These are often, but not always, associated with replicated yield trials.

Pod shatter loss is the amount of seed lost from shattered pods at harvest; seeds are collected in three 7"×13" pans placed 3' from either end or at center of each plot and converted to kg/ha.

Pod shatter resistance, or shatter resistance, means the resistance to silique shattering observed at seed maturity. 1=not tested, 3=poor, 5=fair, 7=good, 9=does not shatter.

Pod (silique) Beak length, measured in mm, for 30 pods taken per plot, from pods occurring on mid-third of the main raceme.

Pod (silique) length is the length of the pod not including the pedicel or beak, measured in mm, for 30 pods per plot taken from the mid-third of the main raceme.

Pod (silique) width is the typical pod width when mature, for 30 pods per plot taken from the mid-third of the main raceme. Rating scale is typically categorical: 3=narrow; 5=medium, 7=broad.

Primary raceme length, measured in cm, means the measurement of the main raceme from the last (youngest) branch to the top of the inflorescence. This measurement often taken from end flowering to full pod set stage of plant development.

Progeny refers to plants derived from a plant of *Brassica carinata* variety Nujet 400. Progeny may be derived by regeneration of cell culture or tissue culture of a plant of carinata variety Nujet 400, self-pollination of a plant designated Nujet 400, crossing at least one plant of *Brassica carinata* variety Nujet 400 with a plant of another variety or line of *Brassica carinata* or other Brassicaceae species, or by producing seeds of a plant of *Brassica carinata* variety Nujet 400.

Protein content means the typical percentage by weight (wt %) of protein in the oil-free meal of the mature whole dried seeds, at less than 6% moisture, analyzed using near infrared (NIR) spectroscopy (AOCS Procedure Am 1-92 Determination of Oil, Moisture and Volatile Matter, and Protein by Near-Infrared Reflectance).

Randomized Complete Block Design (RCBD) is the most common experimental design used in standard replicated yield testing, typically consisting of four replications of various breeding lines or varieties, having the complete set of entries arranged in different randomizations for each replication.

Recovery from frost damage, is assessed by rating the same plots at a couple additional time points beyond the initial rating, often at two and three weeks following a hard frost event.

Regeneration means the development of a plant from cell culture or tissue culture or vegetative propagation.

Replication refers to a series of ratings or observations, taken from different plots or samples of the same variety, breeding line, or trait thereof, from plants grown at the same location or within a given set of trials. Replicated measurements are critical for greater accuracy in statistical analysis.

Resistance means the ability of a plant to withstand exposure to an insect, disease, herbicide or other potentially stress-inducing condition. A resistant plant variety or hybrid will have a level of resistance higher than a comparable check variety or hybrid.

Saturated Fatty Acids refer to Fatty Acids in which carbon chains are linked by single bonds; they lack unsaturated links between carbon atoms. The Saturated Fatty Acid content of oil in the seed is the sum total of all such Fatty Acids expressed as a percentage by weight as a proportion of all Fatty Acids.

Sclerotinia resistance is the level of resistance of varieties or breeding lines to Sclerotinia Stem Rot, a common fungal disease in Brassica crops caused by the pathogen *Sclerotinia sclerotiorum*. It is typically rated on a scale from 0-5; 0=no symptoms were observed, 1=infection of pods only, 2=disease prevalence on 25% of upper plant, 3=50% prevalence, 4=75% prevalence, and 5=disease symptoms are seen throughout entire plant and considered severe.

Seed colour (NIR), means the seed coat colour of typical mature seeds based on NIR analysis. For this objective measurement, the colour of an aggregate sample of seed (1-5 g of seed) is determined by using the FOS XBR, or equivalent, near infrared spectrophotometer as a reflectance spectrophotometer over the visible range (400 nm to 700 nm) to provide an objective description of the carinata seed color, essentially as described (Black and Panozzo, 2004) except that seed color is described in terms of the Hunter L*A*B* color space rather than CIEL*A*B* color space.

Seed colour (visual), is a subjective categorization of the predominant seed coat colour at seed maturity for a given variety or breeding line. These are generally grouped into the following categories: Y=Yellow or bright yellow; DY=Dark yellow; LB=Light brown; B=Brown; DB=Dark brown; O=Orange.

Seed Maturity refers to number of days from planting to the stage when 70-80% seeds on main raceme had seeds with complete colour change and hard when pressed between fingers.

Seeds per pod, means the average number of seeds per pod, in at least 30 pods taken from the mid-third of the main stalk.

Seed weight (thousand seed weight, or TKW), means the weight, in grams, of 1,000 typical seeds determined at maturity, as measured at a seed moisture content of approximately 5-6%.

Self-pollination or "selfing" means the self-pollination of a plant by transfer of pollen from an anther to a stigma of the same plant. Carinata is a self-compatible species, meaning there are no genetic or physiological impediments to successful self-pollination.

Stand is the number of plants counted in 4 rows and converted to plants/m$^2$. This is most often recorded early in the season, after germination and establishment, or late in the season just prior (2-4 days) to harvest.

Stem colour refers to the predominant stem colour at bolting stage, depending on levels of anthocyanin manifest in the stem. This is generally categorical, characterized as G=Green; LP=Light Purple; and P=Purple or dark purple.

Tissue culture refers to a composition comprising isolated cells of the same or a different type or a collection of such cells organized into part of a plant. This technique is an integral part of breeding techniques such as doubled haploidy, whereby new diploid plants of a unique, homozygous genetic composition are generated in lab conditions to the point where normal plant growth can occur in the field or in a greenhouse.

Tolerance is commonly used in the context of plants affected by abiotic stress, diseases, or pests and is used to describe an improved level of field resistance.

Traditional plant breeding techniques include, but are not limited to, crossing, selfing, selection, double haploid production, embryo rescue, marker assisted selection, mutation breeding, backcross breeding, single seed descent, and any other method known to the breeder other than genetic modification and transformation/transgenic methods, by which a genetically heritable trait can be transferred from one carinata line or variety to another, or traits of interest fixed in one genetic background.

Trait introgression refers to plants within a variety have been modified in a manner that retains the overall genetics of the variety and further comprises one or more loci with a specific desired trait, such as male sterility, disease, or herbicide resistance. Backcrossing followed by inbreeding or DH line generation is a common methodology to achieve this objective. Using this technique, one or more value added traits may be introduced into a single carinata variety.

Transgene means a genetic locus comprising a DNA sequence which has been introduced into the genome of a *Brassica carinata* plant by transformation. A plant comprising a transgene stably integrated into its genome is referred to as a transgenic plant.

DETAILED DESCRIPTION

In one aspect, the present invention relates to cells, seeds, plants, and plant parts of *Brassica carinata* variety Nujet 400, alternatively "carinata variety Nujet 400", "variety Nujet 400", or "Nujet 400", for which a representative sample of the seed has been deposited under ATCC Accession number PTA-127252.

In another aspect, the present invention relates to *Brassica carinata* plant or plant part produced or derived from seeds, plants, and plant parts of *Brassica carinata* variety Nujet 400, as well as to all progeny of *Brassica carinata* variety Nujet 400 produced by one or more breeding, mutagenesis, tissue culture, or genetic modification techniques and having essentially all the physiological and morphological characteristics of a plant or plant part of *Brassica carinata* variety Nujet 400 when grown in the same location under the same environmental conditions as variety Nujet 400.

In another aspect, the present invention relates to *Brassica carinata* plant or plant part produced or derived from seeds, plants, and plant parts of *Brassica carinata* variety Nujet 400, as well as to all progeny of *Brassica carinata* variety Nujet 400 produced by one or more breeding, mutagenesis, tissue culture, or genetic modification techniques and having the physiological and/or morphological characteristics set forth in one or more of Tables 1, 2, 3, 4, 5, 6, 7, and 8, as determined at the 5% significance level, when grown in the same location under the same environmental conditions as *Brassica carinata* variety Nujet 400.

The present invention also relates to any plants produced or derived from seeds, plants, and plant parts of *Brassica carinata* variety Nujet 400, that exhibit "carinata character".

For the purpose of the present invention, plants exhibiting "carinata character" have an erect, upright bearing, are highly branching, with well-developed and aggressive tap root systems (Barro and Martin, 1999). Leaves are generally wide elliptic in shape with weak-medium dentation, medium glaucosity, and very sparse pubescence. Seeds are globose, 1-1.5 mm in diameter and finely reticulated (Mnzava and Schippers, 2004) and vary from yellow to yellow-brown to brown in colour (Getinet 1987; Rahman and Tahir, 2010).

Plants exhibiting "carinata character" may be produced from the seed of *Brassica carinata* variety Nujet 400; a representative sample of the seed has been deposited under ATCC Accession number PTA-127252 or from any cell, plant or plant part produced from the seed of *Brassica carinata* variety Nujet 400, using one or more (conventional) plant breeding technologies, cell culture or tissue culture technologies, and/or transgenic technologies.

Plant Breeding Technologies

Critical to the development and breeding of any crop is the ability to make use of genotypic and phenotypic diversity. Breeding strategies make use of the plant's method of pollination: self-pollination, where the pollen from one flower is transferred to the same or another flower on the same plant or a genetically identical plant; sib-pollination, when individuals with the same family or line are used for pollination; or cross-pollination, where the pollen comes from a flower on a genetically different plant from a different family or line.

For practical application, a breeder initially selects and crosses two or more parental lines, followed by repeated selfing and selection to produce many unique genetic combinations. For a newly developing crop such as carinata, it is necessary to be able to obtain a sufficient pool of genetic material to identify genetic backgrounds more adapted to target geographies (i.e. a better starting point), as well as variation for traits of interest. This allows for crossing or other modifications to be done to identify genetic combinations superior to the types already tested. Thus, an important initial objective is the collection and characterization of as large of a collection of genetic backgrounds as possible, for each target geography. Parental lines are selected based on breeding priorities and the unique combination of traits available in potential crossing parents. The selection of parents of these crosses is critical to the effectiveness of a breeding program. Parental lines may be closely or distantly related lines of a single plant species or may be two different species of the same genus.

Crossing, of (inbred) parental lines, by sexual hybridization, is typically done manually in controlled conditions. Often, two or three rounds of crossing are needed to accumulate beneficial alleles into a single genetic background. This includes evaluating offspring of a cross, selecting the most desirable (inbred) lines as future parents, and making the next round of parental selection based on priority targets. Theoretically, billions of different genetic combinations can be produced through a combination of mutagenesis, selfing, and crossing. Since the breeder has no direct control at the cellular level, two breeders will never independently develop the same variety of carinata plants having precisely the same traits and genetic composition.

In each cycle of selection and evaluation, the breeder selects germplasm to advance to the next generation by growing individual plants in the chosen geography, soil and climate conditions and collecting phenotypic data reflective of actual performance that would be realized by a seed producer. Traits collected focus on those that would be of agronomic or economic benefit in the crop. Examples of traits characterized in a carinata breeding program include, but are not limited to, early plant vigor, plant height, branching habit, days to flower, silique density, flower petal color, pod size, reaction to heat and water stress, disease susceptibility, and pod shatter tolerance.

In a typical carinata breeding program, the breeder initially selects and crosses two or more parental *Brassica carinata* lines, followed by repeated selfing and selection to produce many unique genetic combinations, which are evaluated for overall agronomic potential as well as specific traits. Such recurrent selection can be used to improve a population of either self- or cross-pollinating *Brassica*. Intercrossing of several parents creates a genetically variable population of heterozygous individuals and the best plants are selected based on individual superiority, outstanding progeny and/or excellent combining ability. New populations are created by further intercrossing and selection. This method is useful for the improvement of quantitatively inherited traits controlled by numerous genes.

Backcrossing may be used to transfer genes for a simply inherited, highly heritable trait from a donor parent to the recurrent parent. After the initial cross, individual plants with the desired trait of the donor parent are selected and backcrossed to the recurrent parent for several generations. The resulting progeny are expected to have the attributes of the recurrent parent and the desired trait from the donor parent. Backcrossing may be used in conjunction with pedigree breeding. Pedigree breeding and recurrent selection methods are used to develop varieties from breeding populations. Pedigree breeding starts with the crossing of two genotypes, each with one or more desirable characteristics that is lacking in the other or that complement each other. Additional genotypes can be included in the breeding population if the original parents do not provide all the desired characteristics. In the pedigree method of breeding, five or more generations of selfing and selection may be used. For example, crossing of the two initial parents (the donor and recurrent parents) produces an initial F1 population, from which an F2 population is produced by selfing one or several F1 plants or by intercrossing two F1 plants (sib mating). Development of inbreds with desired combination of traits may be conducted starting with the F2 population, or with the F3 or subsequent population.

Plants that have been self-pollinated and selected for several generations become homozygous at nearly all gene loci and produce a uniform population of breeding progeny or inbred lines. Subsequent crosses with two different homozygous (inbred) lines produces a uniform population of hybrid plants that may be heterozygous for many gene loci (standard F1 hybrid production). These types of hybrids are reproducible from the inbred parental line genotypes. Crossing two plants each heterozygous at a number of gene loci will produce a population that differ genetically and will not be uniform.

Doubled haploid (or DH) technology allows for the generation of completely homozygous lines, which are a combination of genes of the parental lines, in a single generation. This accelerates the process of inbred line development dramatically as the process from seeding of parental lines to obtaining seed for a resulting inbred population from those parents will generally take about 18 months. To achieve a highly homozygous line using traditional self-pollination generally will take five or six growth cycles which, in the case of carinata, would represent three years or six growth cycles, with two cycles completed per year. In DH technology, using appropriate in vitro conditions, haploid microspores from an F1 plant can be induced to differentiate into diploid embryos and subsequently plantlets. This technique typically relies on a percentage of regenerated plants to undergo spontaneous doubling (usually in the range of 20 to 60% of plants, depending on several factors), whereas the remaining plants will remain haploid and sterile. To increase the efficiency of space used for seed increase, such as in the greenhouse or field, a flow cytometer is used to distinguish at an early stage the chromosome content "n" or "2n" of each plant. Thus, the sterile plants can be discarded at an early stage.

In some instances, a desirable trait may not reside within the species of interest, specifically *Brassica carinata*. In that case, it may be possible to transfer the trait via interspecific or wide crossing. For interspecific crossing, one parent is *Brassica carinata* variety Nujet 400 and the second parent may be a different species of *Brassica*, including but not limited to *B. juncea* (L). Czern. (brown mustard), *B. napus* L. (rape, Argentine canola), *B. nigra* (L.) W. D. J. Koch (black mustard), *B. rapa* L. (field mustard, Polish canola), and *B. oleracea* L. (cabbage, broccoli, cauliflower, brussels sprouts, kohlrabi and kale). In other instances, the other Brassicaceae species including but not limited to *Brassica alba, Brassica hirta, Brassica juncea, Brassica napus, Brassica nigra, Brassica oleracea, Brassica rapa, Sinapus alba*, and *Camelina sativa.*

The methodology for performing interspecific crosses is similar to that described for within-species crosses described above. However, unlike intraspecific crosses, the likelihood that the resulting progeny will produce viable seed is very low and thus represents a formidable challenge to the success of this technique. To overcome this potential block, embryo rescue techniques are often employed to recover viable offspring from the cross. Essentially, this relies on the progeny surviving until the embryogenic stage at which point it can be dissected from the silique and placed into artificial growth medium. Under appropriate conditions, the cultured embryo can survive and be induced to differentiate into a plantlet, which can be grown into a mature plant. Successive rounds of embryo rescue may be needed until inbred progeny, or backcross-derived progeny, are stable and can produce fertile offspring without intervention. Often molecular markers, where available, are used to trace a specific allele from a related species into an adapted background in the target species, using repeated cycles of backcrossing.

In addition, to minimize the relative proportion of the donor genome from the non-carinata species, several rounds of back-crossing of the rescued plants with the *Brassica carinata* parent may be required to generate progeny having carinata character and the desired trait, which are stable and can produce fertile offspring.

Selection

Breeding nurseries are often the first cycle of evaluation of breeding populations. Generally, nurseries utilize single or paired rows with frequent checks (i.e. the best available commercial germplasm for a specified geography).

Various methods are used to screen breeding populations for individual plants with desired characteristics. Single seed descent procedure refers to planting a segregating population, harvesting a sample of one seed per plant, and using the one-seed sample to plant the next generation. When the population has advanced from the F2 to the desired level of inbreeding, the plants from which lines are derived will each trace to different F2 individuals. Since the number of plants in a population declines each generation due to failure of some seeds to germinate or produce seed, not all the F2 plants will be represented by a progeny in the final generation.

A plant-to-row selection method is when seed from a single, self-pollinated plant selected from a segregating population is used to generate another row in the next cycle of observation nursery and selection. This process is repeated until the resulting breeding lines have a high level of homogeneity and homozygosity. If desired, at any given point along the selection process, Double(d) Haploid methods can be used to extract homogeneous (homozygous) lines.

Marker Assisted Selection and Marker Assisted Breeding

A breeding program can make use of marker assisted selection (MAS) and marker assisted breeding (MAB) technologies to accelerate the successful outcome of a breeding project. These techniques enable the identification of lines carrying a trait of interest in the laboratory, while other lines not containing a marker of interest can then be discarded at an early stage. These methods can also increase the efficiency of a program, as the lines being evaluated in the field have a greater probability of meeting seed quality or other criteria. MAS and MAB methods rely on the existence of a dense set of genetic markers for the species of interest. Genetic markers are the unique sequences that may be found in allelic forms of genes, distinguishing one allele from another. Like genes themselves, they can be transmitted to progeny in a Mendelian fashion and can thus be used to follow the movement of specific alleles from parents to progeny.

Molecular markers can be used in Quantitative Trait Loci (QTL) mapping whereby selection of plants with desired trait(s) is assisted by markers known to be closely linked to alleles that have measurable effects on a quantitative trait—i.e., accumulation of markers linked to positive effecting alleles or elimination of markers linked to negative effecting alleles in the plant genome. Markers can also be used to select for the genome of the recurrent parent and against the markers of the donor parent. This can minimize the amount of genome from a donor parent that remains in the selected plants and/or the number of back crosses to the recurrent parent.

Other types of genetic markers in common use by persons skilled in the art include, but are not limited to, Restriction fragment length polymorphisms (RFLP), Random Amplified Polymorphic DNA (RAPD), Amplified Fragment Length Polymorphism (AFLP), Arbitrarily Primed Polymerase Chain Reaction (AP-PCR), DNA Amplification Fingerprinting (DAF), Sequence Characterized Amplified Regions (SCARs), Simple Sequence Repeats (SSRs), and Single Nucleotide Polymorphisms (SNPs).

Mutagenesis

Another method of creating genetic variation and capturing beneficial changes in a heritable fashion is through mutagenesis breeding. This method is often carried out via chemical means or ionizing radiation and is typically focused either on a microspore or on a whole seed level. In *Brassica* breeding, some common forms of mutagens used have been chemical agents such as ethyl methanesulfonate (EMS) or N-ethyl-N-nitrosourea (ENU), or high levels of ionizing radiation (x-ray or gamma irradiation or exposure to UV light). EMS produces random point mutations via low frequency methylation of guanine residues in genomic DNA. This results in altered Watson-Crick base pairing such that the affected base pairing is converted from G-C to A-T. ENU is also an alkylating agent that preferentially modifies thymine residues converting A-T to G-C. Ionizing radiation may affect DNA in many ways but typically the mutations are double strand breaks leading to deletions and frameshift mutations that are frequently inactivating.

To carry out this technique, seedlings or microspores are exposed to the mutagenic agent and the surviving fraction are allowed to develop into mature plants. In some cases, the mutagenized plantlets or embryos (in the case of microspore mutagenesis) may be exposed to selection in order to enrich for a particular phenotype. For example, mutagenesis has been used to develop plants that are resistant to the actions of specific herbicides; in this instance the developing plantlets or microspores can be grown in vitro in the presence of the herbicide(s) of interest in order to select for those plants with the appropriate mutations conferring resistance. The advantage of the microspore mutagenesis of the seed approach is that the resultant DH plants can be used to derive pure and homozygous plant lines where all induced mutations, whether dominant or recessive, would be expressed. Mutagenesis has been used to develop Brassica varieties with resistance to various herbicides, altered seed oil profiles and increased tolerance to disease and abiotic stress.

Genetic Transformation and Transgenic Technologies

In instances where unique and valuable traits are known to be available in distant plant or in non-plant species that cannot be transferred to *Brassica carinata* via classical breeding, and where the genes for those traits have been cloned, a breeding program may employ genetic transformation techniques, or transgenic technologies, to stably transfer those genes into this species. Transfer of cloned genetic elements into *B. carinata* have been achieved via a number of means, including PEG-mediated DNA uptake into protoplasts (Johnson, et al., 1989), electroporation into protoplasts (Fromm, et al., 1985), ballistic infiltration using DNA coated microprojectiles (Finer, et al., 1999), *Agrobacterium*-based vector infiltration (Babic, et al., 1998), and infection using plant virus-based vectors (Gleba, et al., 2004). Aside from having the genes of interest in cloned form, the other requirements include having the genes cloned into a suitable vector to allow for their propagation in an appropriate bacterial system, as well as their packaging in appropriate viral and *Agrobacterium* strains if transformation utilizes an infectious route of transfer. Once transferred, the gene(s) of interest would also require appropriate plant-based promoters, enhancers and terminators to allow for the correct temporal and tissue specific pattern of expression for the heterologous gene. Finally, to select for those rare events where the heterologous gene expression unit has been successfully transferred into the plant genome, a selectable marker may be introduced, either physically linked to the heterologous gene of interest or co-transformed with the gene of interest at a suitable ratio to favor co-insertion.

The selectable marker may consist of a gene that can confer resistance to a particular herbicide or antibiotic that would otherwise kill the plant, a gene that may confer a growth advantage, a gene that may alter a response to plant hormones, or a gene that expresses a fluorescent protein that can allow transformed cells to be easily visualized. Examples of selectable markers conferring resistance to antibiotics that have been successfully used in *Brassica* transformation are the NPTII gene (Bevan 1984; Datla, et al., 1992), encoding an enzyme conferring resistance to the antibiotic kanamycin, and the HPT gene encoding an enzyme conferring resistance to the antibiotic Hygromycin (Rothstein, et al., 1987). Examples of selection markers based on conferring tolerance to herbicides and successfully used in *Brassica* transformation are the BAR (Thompson, et al., 1987) and PAT (Wohlleben, et al., 1988) gene products, which encode phosphinothicine acetyltransferase and confer resistance to glufosinate (bialaphos) or L-PPT, and the AHAS gene product encoding acetohydroxyacid synthase enzyme conferring resistance to imidazolinones (Miki, et al., 1990). Other plant selectable markers have been developed whose actions are not based on conferring resistance to toxic compounds per se but instead allow survival in the presence of nutrients not normally metabolized by the wildtype organism.

Transformation cannot only be used to introduce heterologous genes into the genome of carinata plants, it can also be used to introduce nucleic acid constructs that are designed to modulate the expression of endogenous genes. Nucleic acid constructs encoding antisense RNA or RNAi sequences (Tang and Galili, 2004) can be used to interfere or knock down the expression of endogenous genes to extremely low levels, simulating the effect of a null mutation at the endogenous locus. This of course relies on the continuous stable expression of the antisense RNA or RNAi to be effective. In amphidiploid *Brassica* species such as *napus, juncea* and *carinata*, multiple copies of genes from the contributing ancestral species may create a high level of functional redundancy such that a single mutation in one of the homologues may not be sufficient to confer a phenotype. However, by using an RNAi or antisense approach, where the interfering RNA is derived from conserved sequences, one may conceivably be capable of targeting all the expressed homologues and achieving a functional knock-down effect.

Examples of modifications that can be introduced into *Brassica carinata* using genetic transformation include, but are not limited to,

- genes that control pollination, hybrid seed production, or male-sterility;
- genes encoding resistance to pathogens and insect pests (plant disease resistance gene(s); gene(s) conferring resistance to fungal pathogens; natural or synthetic *Bacillus thuringiensis* (Bt) protein or a derivative thereof; an insect-specific hormone or pheromone coach or a mimetic based thereon, or an antagonist or agonist thereof; an insect-specific peptide that disrupts the physiology of the affected pest; an enzyme responsible for hyperaccumulation of a non-protein molecule with insecticidal activity; a membrane permease, a channel former or a channel blocker; a viral-invasive protein or a complex toxin derived therefrom; an insect-specific antibody or an immunotoxin derived therefrom; genes involved in the Systemic Acquired Resistance (SAR) Response and/or the pathogenesis related genes; antifungal genes; detoxification genes, such as for fumonisin, beauvericin, moniliformin, and zearalenone, and their structurally related derivatives; cystatin and cysteine protease inhibitors; Defensin genes; genes that confer resistance to Phytophora Root Rot, such as the Brassica equivalents of the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7, and other Rps genes);
- genes that confer resistance to a herbicide (mutant ALS and AHAS enzymes to confer resistance to imidazolinone or sulfonylurea herbicides; mutant 5-enolpyruvylshikimate-3-phosphate synthase (EPSP) and aroA genes conferring resistance to glyphosate; phosphinothricin acetyl transferase (PAT) and *Streptomyces hydroscopicus* phosphinothricin-acetyl transferase (BAR) conferring resistance to other phosphono compounds such as glufosinate; ACCase inhibitor-encoding genes conferring resistance to pyridinoxy or phenoxy propionic acids and cyclohexones; pabA and gs+ genes conferring resistance to triazine; nitrilase gene conferring resistance to benzonitrile; acetohydroxy acid synthase, which has been found to make plants resistant to multiple types of herbicide);
- genes that confer or contribute to altered fatty acids (down-regulation of stearoyl-ACP desaturase to increase stearic acid; elevating oleic acid via FAD-2 gene modification and/or decreasing linolenic acid via FAD-2 gene modification; altering conjugated linolenic or linoleic acid content; altered LEC1, AGP, Dek1, Superall, mi1 ps, various lpa genes such as lpa 1, lpa3, hpt, or hggt);
- genes that confer or contribute to altered phosphorus content (introduction of a phytase-encoding gene; up-regulation of a gene that reduces phytate content);
- genes that confer or contribute to altered carbohydrates, antioxidant, or essential seed amino acids;
- genes that create a site for site specific DNA integration, such as the introduction of FRT sites that may be used in the FLP/PRT system and/or Lox sites that may be used in the Cre/Loxp system;
- genes that affect abiotic stress resistances (including, but not limited to flowering, pod and seed development, enhancement of nitrogen utilization efficiency, altered nitrogen responsiveness, drought resistance or tolerance, cold resistance or tolerance, and salt resistance or tolerance, and increase yield under stress).

Gene Editing

More recently, several novel approaches have been developed which offer the ability to manipulate the plant genome in a targeted way. Collectively known as gene editing technology (Petolino, et al., 2010; Woo, et al., 2015, Sauer, et al., 2016), the technologies share several important similarities:

- they offer the ability to introduce small or large gene deletions or insertions in the plant genome by means of targeted double strand breaks at precise genomic locations;
- they allow for the insertion of small inactivating mutations into specific genes of interest;
- they permit the replacement of an entire gene or gene segment by a modified counterpart;
- they allow for the insertion of a heterologous gene in a specific genomic location which may represent a preferred site for regulated gene expression. (i.e. downstream of a known endogenous promoter/enhancer).

Locus Conversion

The *Brassica carinata* variety described herein represents a new base genetic line into which a new locus or trait my be introduced using transgenic technologies or back-crossing. The term “locus conversion” refers to the product of such an introgression. For example, a donor parent having a specific desirable trait may be crossed with an inbred variety, the recurrent parent, which has overall good agronomic characteristics yet lacks the desirable trait. The progeny of this cross is then mated back to the recurrent parent followed by selection of the desired trait from the donor parent.

A locus converted plant cell of a locus converted plant is obtained by introducing one or more locus conversion in the *Brassica carinata* variety described herein. The locus converted plant cell is therefore identical to a cell from the *Brassica carinata* variety described herein except for the one or more locus conversion and the locus converted plant exhibits essentially all the physiological and morphological characteristics of the *Brassica carinata* variety described herein. The locus conversion can confer a trait selected from the group consisting of male sterility, disease resistance, fungal resistance, pest resistance, herbicide tolerance, abiotic stress tolerance, and altered metabolism. Both naturally occurring and transgenic DNA sequences may be introduced through backcrossing. Molecular marker assisted breeding or selection maybe use used to reduce the number of backcrosses need to achieve the backcross conversion.

A locus conversion of the *Brassica carinata* variety described herein will otherwise retain its genetic integrity. For example, a locus converted plant of the *Brassica carinata* variety described herein will comprise at least 92%, 93%, 94%, 95%, 96%, 97%, 98% or 99% of its base genetics of the starting variety. A locus converted plant of the *Brassica carinata* variety described herein will therefore have at least one, and possibly two or three physiological or morphological characteristics which are different from those of a locus converted plant of the *Brassica carinata* variety described herein and otherwise has all the physiological or morphological characteristics of a locus converted plant of the *Brassica carinata* variety described herein.

Male Sterility

To produce and test hybrid combinations, some form of pollination control system must be employed. The most widely used pollination control system to achieve this in *Brassica* species is the method of Ogura (Ogura, 1968) adapted and modified by scientists at INRA, which is based on control of pollination by use of male cytoplasmic sterility. In cytoplasmic male sterile (CMS) plants, a mitochondrial gene mutation interferes with the flower's ability to produce viable pollen but does not affect the functionality of the flower's female components. Because the mutation is within the mitochondrial genome, it is transmitted maternally through the cytoplasm. CMS plant lines, termed A lines, can only produce viable seed via outcrossing with non-CMS plants; however, the F1 plants derived from the seed of such a crossing will also exhibit the CMS phenotype and will still not produce viable seed by self pollination.

The Ogura CMS trait, originally identified in Japanese radish varieties (Ogura, 1968), was transferred to *Brassica oleracea* via backcrossing (Bannerot, et al., 1977) then subsequently transferred to *Brassica napus*. These initial *Brassica napus* A lines were found to be deficient in terms of their sensitivity to cold and their tendency to exhibit leaf chlorosis, as well as fertility issues, which were ultimately found to be related to interactions with chloroplasts derived from the radish cytoplasm (Pelletier et al., 1983). Using a cell fusion approach, improved *Brassica napus* A lines were subsequently developed that overcame these initial deficiencies (Pelletier, et al., 1987). A-lines can be maintained by crossing them with B lines (lines that are genetically identical to A lines except that their cytoplasm is not CMS).

For production of fully fertile hybrid seed, CMS lines must be crossed with lines that contain a restorer function gene (Rf) which can restore the ability of CMS plants to produce viable pollen. Plant lines with the Rf function stably incorporated and homozygous (termed R lines) can be crossed with CMS lines and the F1 seed harvested from the CMS plants will represent a true hybrid and which will have the ability to produce fully fertile offspring capable of self pollination, a prerequisite for commercial grain production.

Such an Rf activity, first identified in radish, was introduced into *Brassica napus* (Heyn, 1976). It was subsequently shown that these lines were affected by fertility problems (Heyn, 1978; Pellan-Delourme and Renard, 1988). Intensive backcrossing of these initial lines eventually yielded material with improved fertility such that they could be used practically as Rf lines (Delourme, et al., 1991). It was further noted, however, that hybrid seed produced from crosses with the early versions of *Brassica napus* Rf lines often had high glucosinolate levels (Delourme, Foisset et al., 1998) that made generation of canola quality hybrids problematic. Efforts to develop improved Rf lines by reducing the amount of extraneous radish genetic material has resulted in newer generations of *Brassica napus* (Primard-Brisset, et al., 2005) and *Brassica juncea* (Tian, et al., 2014) Rf line families of sufficiently quality to be used in commercial hybrid seed production. Seed of Rf lines can be maintained by allowing self crossing of plants grown in isolated tents or fields.

A, B and R lines are thus the prerequisite components of an expandable production system for F1 hybrid seed. In practice, for production of pure hybrid seed:

a. the hybrid production fields are required to be reproductively isolated from extraneous sources of *Brassica* pollen;
b. R lines are seeded at a predetermined optimal ratio relative to A lines and may be kept spatially separated from the A lines so that the Rf plants can be readily removed post flowering, and prior to harvest of the A line material;
c. pollinators are absolutely required to allow for maximal pollination of the A lines by CMS pollen donors;
d. for maintenance and expansion of R line stocks, Rf seed is planted in isolation (either isolated fields separated from other *Brassica* crops by great distance, or plots that are reproductively isolated by virtue of a physical barrier such as a tent) and allowed to self pollinate;
e. for maintenance and expansion of A line stocks, A lines and B lines are planted in separate rows in isolated fields or tents (as described above) and pollinators are used to promote pollination of A lines with B line pollen. B lines are cut down after flowering and before seed set and the A line plants are allowed to come to maturity then harvested.

In some cases, a less labor- and cost-intensive alternative to that described in (b) is employed whereby a low ratio of Rf plants may be interspersed with the A line plants in the field and harvested together. While there will be some level of adulteration of the harvested hybrid grain with that of the self-pollinated Rf plants; however, in practice this level of contamination will not greatly affect the commercial quality of the hybrid seed.

More recently, both the CMS and Rf traits have been transferred to *Brassica carinata*. The development of a set of genetically diverse CMS and Rf lines in *Brassica carinata* allows the testing of many combinations for the first time in this *Brassica* species.

In a hypothetical test scheme based on the Ogura CMS system, the following steps are carried out:

- panels of genetically diverse *Brassica carinata* varieties are selected from a previously characterized collection of elite germplasm and used for introgression of CMS or Rf traits to produce A and R test lines. Diversity can be estimated by comparing differences in molecular marker profiles between candidate lines;
- crosses are carried out between selected diverse A and R test lines, under conditions described in previous sections;
- F1 carinata hybrid seed from test crosses are planted in replicated small plot trials, F1 plants and harvested seed are assessed for a number of traits including, but not limited to, early vigour, yield potential, grain and oil yield per acre, as well as seed quality traits;
- patterns of heterosis between pairs A and R parents are identified and F1 hybrid seed from promising combinations are studied more extensively in larger, geographically diverse trials; and
- hybrid seed from specific combinations may be selected for potential commercial release as a new variety.

Phenotype/Genotype

To be useful and reliable, a *Brassica carinata* variety or hybrid must be homogenous and reproducible. While there are a number of analytical methods known to the skilled person for assessing the phenotypical stability of a *Brassica carinata* variety or hybrid, the traditional method is the observation of phenotypic traits over the life of the carinata plant using data collected from field experiments conducted under the selected geographic, climatic, and soil conditions during one or more growing seasons. Phenotypic characteristics observed include, but are not limited to, traits associated with seed yield (pod density, number of seeds per pod, pod length), oil yield, seed oil quality (GSL and erucic acid content; fatty acid composition), seed protein content, seed protein quality, glucosinolate composition of meal, growth habit, lodging resistance, plant height, and pod shatter resistance. Other phenotypic characteristics that may be observed include, but are not limited to, traits associated with pest tolerance or resistance, cold or frost tolerance, disease tolerance or resistance, herbicide tolerance or resistance, early or late flowering, and/or early or late maturity.

In some embodiments, *Brassica carinata* varieties or hybrids useful for commercial crop production or production of commercial products may exhibit traits associated with seed yield, oil yield, seed oil quality, erucic acid content of seed or oil, glucosinolate content of seed, seed protein content, fatty acid composition of oil, glucosinolate composition of meal, meal protein content, growth habit, lodging resistance, plant height, and pod shatter resistance.

In some embodiments, a *Brassica carinata* variety or hybrid may exhibit multiple traits or phenotypic characteristics that provide agronomic advantages in particular geographies, climates, cropping regimes, and/or soil types. For example,

- *Brassica carinata* varieties for planting in regions with a climate classified as being of tropical moist or humid subtropical characteristics, with planting occurring in fall or winter for harvest in spring or summer, may be selected for one or more traits including, but not limited to, superior yield of oil per area planted, shorter time to maturity, improved frost tolerance, improved disease resistance, nitrogen use efficiency, resistance to plant lodging, and resistance to pod shatter.
- *Brassica carinata* varieties for planting in regions with a climate classified as being of cool temperate, dry classification, with planting occurring in spring and harvest in summer or fall, may be selected for one or more traits including, but not limited to, superior yield of oil per area planted, shorter time to maturity, tolerance to drought, improved disease resistance, and resistance to pod shatter.
- *Brassica carinata* varieties for planting in regions with a climate classified as being of warm temperate, moist characteristic for planting in fall or winter for harvest in spring or summer, may be selected for one or more traits including, but not limited to, superior yield of oil per area planted, shorter time to maturity, tolerance to drought, improved disease resistance, nitrogen use efficiency, resistance to lodging, and resistance to pod shatter.

Other traits for which *Brassica carinata* varieties may be selected include, but are not limited to, *Alternaria* resistance, days to flowering, depth of canopy, duration of flowering, end of flowering, flower petal coloration, frost tolerance, herbicide resistance, leaf colour, leaf glaucosity, leaf length, leaf number of lobes, leaf width, maturity, seed maturity, number of seed-bearing pods, pod (silique) beak length, pedicel length, petiole length, plant height, plant length, pod (silique) length, pod (silique) width, primary raceme length, recovery from frost damage, *Sclerotinia* resistance, seed colour, seeds per pod, seed weight (thousand seed weight or TKW), and stem color.

Genotype assessment(s) can be used to confirm the homogeneity and reproducibility of a *Brassica carinata* hybrid, to identify plants of the same variety or related variety, and to confirm the pedigree of the plant. Techniques known to those skilled in the art for the analysis and comparison of plant genotype include, but are not limited to, whole genome sequencing, Restriction fragment length polymorphisms (RFLP), Random Amplified Polymorphic DNA (RAPD), Amplified Fragment Length Polymorphism (AFLP), Arbitrarily Primed Polymerase Chain Reaction (AP-PCR), DNA Amplification Fingerprinting (DAF), Sequence Characterized Amplified Regions (SCARs), Simple Sequence Repeats (SSRs), and Single Nucleotide Polymorphisms (SNPs).

The *Brassica carinata* variety of the present invention has shown uniformity and stability for all traits described in the variety description information in Table 7, which include morphological, agronomic, and quality traits for *Brassica carinata* variety Nujet 400. The detailed phenotypic information provided in Table 7 is based on data collected in field experiments using conventional agronomic practices. For comparative purposes, *Brassica carinata* open-pollinated variety Avanza 641 and canola hybrid variety Nuola 300 were similarly grown as comparative check varieties in replicated experiments, and observations were recorded for the various morphological traits for *Brassica carinata* variety Nujet 400 and the comparative check varieties.

Disease

Varieties of *Brassica carinata* may be susceptible to a number of pathogens that commonly infect *Brassica* species including, but not limited to, the bacteria and fungi listed below:

| Disease | Organism | Disease | Organism |
|---|---|---|---|
| Bacterial leaf spot | *Pseudomonas syringae* | Light leaf spot | *Pyrenopeziza brassicae* |
| Bacterial leaf rot | *Erwinia marginalis* | Powdery mildew | *Erysiphe polygoni* |
| Bacterial soft rot | *Pseudomonas marginalis* | Root rot complex | *Rhizoctonia solani*, *Fusarium* spp., *Pythium* spp. |
| Black rot | *Xanthomonas campestris* | Seeding disease complex | *Rhizoctonia solani*, *Fusarium* spp., *Pythium* spp. |
| Alternaria black spot | *Alternaria* spp | Sclerotonia white stem rot | *Sclerotonia sclerotiorum* |
| Alternaria grey leaf spot | *Alternaria brassicae* *Alternaria brassicola* | Aster yellow | *Phytoplasma* spp. |
| Alternaria pos spot | *Alternaria brassicae* *Alternaria brassicola* | Damping off | *Phytophthora cactorum Pythium* spp. |

-continued

| Disease | Organism | Disease | Organism |
|---|---|---|---|
| Black leg | *Leptosphaeria maculans* *Leptosphaeria biglobosa* | White leaf spot | *Mycosphaerella capsellae* |
| Black root | *Aphanomyces raphanin* | Grey stem | *Mycosphaerella capsellae* |
| Clubroot | *Plasmodiophora brassicae* | Wirestem and girdling root rot | *Rhizoctonia solani* |
| Downey mildew | *Peronospora parasitica* | White rust | *Albugo candida* |
| Fusarium wilt | *Fusarium oxysporum* *Fusarium avenaceum* | Verticillium wilt | *Verticillium longisporum* |

Examples of economically significant fungal diseases of *Brassica* species and mustard oilseeds include a. Sclerotinia stem rot is caused by a fungus whose spores infect *Brassica* species primarily during flowering stages and whose incidence is associated with periods of high humidity. Lesions are formed on the stems which can eventually kill the plant. Fungicides are available which can control the severity of the infection but must be applied at specific periods of the plant lifecycle (i.e. at early to mid-flowering) for best effect. Often multiple applications within this window of time are necessary.

b. Alternaria is a fungal disease of *Brassica* species that affects plants at all growth stages from early seedling through to maturity although mature plants are more susceptible. The greatest economic impact is on grain yield and quality. Foliar fungicide application during the late flowering stage is an effective way to mitigate the more detrimental effects of the disease on grain yield and quality.

c. Blackleg is caused by a fungal pathogen *Leptosphaeria maculans* of *Brassica* oilseed crops, which infects plants at all stages, but early stage infections have the most serious consequences, often culminating in plants with necrotic lesions on their lower stems that can virtually sever the plants at the base. Fungicides are only partially effective, having a minor protective effect when applied at an early plant growth stage.

d. Clubroot is caused by a soil borne fungus-like pathogen (*Plasmodiophora brassicae*) that affects the roots of *Brassica* oilseed crops. The spores can persist for long periods in the soil and there is currently no effective fungicidal treatment. Management may require using rotations which limit the frequency of *Brassica* planting.

The development of disease tolerant or disease resistant carinata varieties is important for achieving high yields of seed, oil, and other products from *Brassica carinata*. Conventional methods for control of microbial disease may employ one or more of chemical control, disease resistance, and culture control procedures such as crop rotation, liming, and use of bait crops.

When producing a commercial crop or a group of cultivated *Brassica carinata* plants in a field, harmful microorganisms can be controlled by the application of a composition comprising one or more microbiocidal ingredients, such as a fungicide. Fungicides comprise a diverse set of chemical agents which can prevent or reduce the severity of plant infection by pathogenic fungi. There are numerous classes of fungicides. FRAC (Fungicide Resistance Action Committee; http://www.frac.info/home) lists 12 classes based on the different biochemical pathways that the fungicides within a class targets, as well as a $13^{th}$ class which comprises fungicides with unknown modes of action. Fungicides are also distinguished by their modes of delivery and sites of action: some fungicides are sprayed onto plant surfaces, some are applied to the soil surfaces either in granular form or as a liquid flooding the soil surface, while others are applied as seed treatments. Fungicides applied to the seeds or soils tend to be absorbed via the roots and are transported to all plant tissues via xylem. Fungicides that are foliar can be either local—i.e., protecting only the surfaces that they contact, systemic—i.e., absorbed by the upper plant surfaces but then transported by xylem to all above ground tissues, or partially systemic—i.e., they can be locally absorbed but can only be transported short distances to protect a somewhat more extensive surface than the initial point of fungicide contact. Fungicides can help mitigate the risk of losses incurred by fungal infection, but the costs of fungicide spraying are significant enough to require cost benefit and risk assessment type analyses to be carried out before deciding to proceed.

When producing a commercial crop or a group of cultivated *Brassica carinata* plants in a field, harmful microorganisms can be controlled by the application of a composition comprising one or more microbicide or fungicide ingredient. Examples of microbiocides and fungicides useful for disease control for *Brassica carinata* include, but are not limited to, azoxystrobin, boscalid, fluxapyroxad, pyraclostrobin, picoxystrobin, propiconazole, metconazole, iprodione, prothiaconazole, vinclozolin, carbathiin, thiram, difenoconazole, metalaxyl, sedaxane, fludioxonil, penflufen, trifloxystrobin, and sedaxane.

Insect Pests

A variety of insect pests may infest and/or cause damage to a developing *Brassica carinata* plant. Common insect pests of *Brassica* at the seedling stage include, but are not limited to, aphids (*Lipaphis erysimi, Myzus persicae, Brevicoryne brassicae*), flea beetles (*Phyllotreta cruciferae, Phyllotreta striolata, Psylliodes punctulata*), cutworm (*Agrotis orthogonia, Euxoa ochrogaster, Feltia jaculifera, Lacimpolia renigrea*), and cabbage root maggot (*Delia radicum*). Common insect pests of *Brassica* at the flowering and podding stages include, but are not limited to, diamondback moth (*Plutella xylostell*), Berta armyworm (*Mamestra configurata*), and cabbage seed pod weevil (*Ceutorhynchus obstrictus*).

When producing a commercial crop or a group of cultivated *Brassica carinata* plants in a field, insect pests may be controlled by the application of a composition comprising one or more insecticide. Insecticides are a group of pesticide compounds designed to reduce or eliminate crop loss due the predation of crop species by insects. Like herbicides and fungicides, insecticides are classified according to their mode of action and the biochemical pathways that they target. One classification scheme (IRAC MoA) advocated by the Insecticide Resistance Action Committee (IRAC; http://www.irac-online.org) lists 29 classes of insecticides grouped by the common biochemical processes and pathways that the insecticide compounds target. Like herbicides and fungicides, insecticide function and persistence can also be influenced by their sites of action, i.e. whether they are only active on the surface of plants as applied, or whether they function as systemic agents. Further differentiation among some insecticide groups may be apparent based on whether they exhibit selectivity for specific insect types due to distinctive aspects of that insect's biology. Given that some insects serve a beneficial role, such as controlling plant pests, serving as plant pollinators and improving the nutrient content of soil, it is important that insecticides not be applied indiscriminately, but rather are used in a way that limits their actions as much as possible to the desired target species. Thus, modalities such as timing of application, amount and route of application, and restrictions on the types of insecticides used and the crops they may be used are all incorporated into the registered usage criteria of insecticide as a means of ensuring their safety and efficacy.

Insecticides useful for the control of insect pests of *Brassica carinata* include, but are not limited to, zeta-cypermethrim, zeta-cypermethrim-S-cyanol, lambdacyhalothrin, methoxyfenozide, cyantraniliprole, imidacloprid, thiamethoxam, and clothianidin. Such insecticide can be applied as a seed treatment or as a foliar treatment.

Plant Pests

*Brassica carinata* is an aggressive crop and will outcompete many weeds if it establishes well. Some weed species, however, if allowed to establish early and persist, can affect quality and yield of all crops, including carinata. Examples of weeds that can adversely affect yield and quality include cochia, wild mustard, and wild radish. Weed management is thus an important aspect of modern agricultural practice and comprises several different but complementary approaches including physical methods to remove weeds before seed can be set, such as cultivation, tilling and rogueing of fields as well as use of chemical agents or herbicides to suppress or kill weedy species before they become established and/or are able to set and release their seed.

When producing a commercial crop or a group of cultivated *Brassica carinata* plants in a field, plant pests can be controlled by the application of a composition comprising one or more herbicide. Herbicides comprise a large group of chemical compounds that interfere with specific biological processes of the plants in such a way as to block their growth and survival. Herbicides are grouped into classes defined by the biological process with which they interact. These can include inhibition of lipid biosynthesis, inhibition of amino acid biosynthesis, hormonal regulation of plant growth, inhibition of photosynthesis, inhibition of nitrogen metabolism, inhibition of plant pigments biosynthesis or function, agents which can disrupt cell membranes and agents which inhibit seedling growth (Sherwani, et al., 2015). In general, different compounds and herbicide classes may display preferential efficacy against certain weedy species. Moreover, some crop species may display more tolerance to certain classes of herbicide than others. Thus, in a particular geographical region, the use of a particular herbicide for weed control may be dictated by the nature of the crop being cultivated and the native weeds encountered in the region. The registered usage also specifies specific methods of application of the herbicide, including recommended concentration of herbicide, use of appropriate diluents, adjuvants, or surfactants, method of delivery (i.e. spray versus granular), timing of application at appropriate crop stage to ensure least crop damage, timing of application and number of applications to ensure optimal weed control, location of application (foliar or soil application), recommended weather conditions for optimal weed control. Some examples of herbicides recommended for use with *Brassica carinata* grown in SE USA are listed (Seepaul, et al., 2015).

Seed Cleaning

"Cleaning (of) seed" or "seed cleaning" refers to the removal of foreign material from the surface of the seed. Foreign material to be removed includes, but is not limited to, fungi, bacteria, insect material (including insect eggs, larvae, and parts thereof), and any other pests that exist on the surface of the seed. "Cleaning (of) seed" or "seed cleaning" also refers to removal of any debris or low quality, infested, or infected seeds, or seeds of different species that are foreign to the sample.

Seed Treatment

Prior to planting, *Brassica carinata* a composition may be applied to the seed as a seed treatment. The composition may be applied at any time from harvesting of the seed to sowing of the seed using methods including, but not limited to, mixing in a container, mechanical application, tumbling, spraying, misting, and immersion. The composition may be applied as a liquid, a slurry, a mist, a soak, or a powder. The composition may comprise one or more of a pesticide, fungicide, insecticide, antimicrobial, a bacterial or fungal inoculant for nutrient utilization, plant growth regulator, or plant signalling compound. A general discussion of techniques for application of fungicides to seeds may be found, for example, in chapter 9 of (Jeffs 1978)

Commercial Crops and Commercial Plant Products

Commercial crop production comprises the steps of seeding, cultivation and harvesting of grain:

- Seeding: *Brassica carinata* can be planted into conventionally tilled soil where conventional tillage or full-tillage comprises a substantial soil inversion repeated several times yearly such that few plant residues remain at the soil surface at the time of seeding. Alternatively, carinata can planted into soil that is maintained under conservation tillage practices whereby the extent and frequency of tillage is substantially reduced with respect to conventional tillage (so-called medium or low tillage soil management) or preferably, it may be no-till planted in standing stubble. Seeding is carried out at a rate designed to achieve plant densities in a range from 60 to 120 plants per square meter. *B. carinata* should be seeded at a consistent 1.25 to 2.5 cm depth. *Brassica carinata* is a mid- to long-season crop that requires a slightly longer growing season than other mustard types. The ideal seeding date depends greatly on geography and weather. In general, soils should be at least 4° C. (40° F.) or higher before planting. In the Canadian Prairies and US northern tier, typical planting occurs in spring between early April to late May. In Southeastern US, typical planting occurs in fall between October and December. In South America, the optimal planting time occurs in early or late fall (i.e. typically between mid April to the end of June).
- Cultivation: For good stand establishment, *Brassica carinata* requires adequate soil moisture at seeding and through emergence but can tolerate reduced moisture thereafter and stands up well to the semi-arid mid-summer conditions. *Brassica carinata* is a temperate climate crop but which has been adapted to the more extreme conditions experienced in the southern Canadian prairies and Northern Tier US states. During initial stand formation, carinata can recover from short term frost conditions and tolerates higher heat during flowering and seed set better than other *Brassica* oilseeds. The fertility requirements of *Brassica carinata* are similar to other mustards and canola. Adequate availability of the primary macronutrients nitrogen, phosphorous, potassium and sulfur are required to achieve the true yield potential. Lesser amounts of secondary macronutrients, including calcium (Ca), magnesium (Mg) and sulfur (S) and trace amounts of micronutrients (such as boron, copper, Iron, manganese, zinc) may also contribute to optimal plant growth and yield. Fertilizer rates vary with growing zone and soil fertility.

Harvesting is the act of collecting the portion of a plant that has matured sufficiently over the course of a growing season and that has value as a source of food, feed, fibre, feedstock, structural material or as a propagule for the plant itself. *Brassica carinata* is harvested, for example, by mechanical harvesting, ideally when seed maturity is reached (seed, pods and stalks turn from green to yellow, seed moisture is 9.5% or less). *Brassica carinata* can be combine harvested by straight cutting or, if need be, can be swathed at an early stage, allowed to dry naturally or with the aid of a desiccant, then the dried swath can be combined. Swathing means cutting near the base of the plant and allowing the plant to lie flat in field for several days to allow the grain to reach the appropriate dryness. However, since *Brassica carinata* has a sturdy stalk, the preferred method for harvest of carinata is direct combining at maturity, rather than swathing or pushing followed by combining.

Combining: refers to the process of reaping and collecting the seed pods from the matured crop, threshing the seed pods to release the seed (grain), and winnowing to separate and recover the grain from the now empty seed pods, stems, and branches (collectively referred to as chaff). These once distinct operations are today often "combined" by use of a multifunctional mechanized apparatus, appropriately known as a "combine" harvester.

Grain, in reference to *Brassica carinata*, refers to the seed harvested at maturity and sold as a source of oil and meal products.

Commercial products produced from *Brassica carinata* seed include, but are not limited to, crushed, non-viable seed, oil, meal, and protein isolate. Production of oil, meal and protein isolate involves multiple steps. Typically, the seeds are cleaned then crushed in a roller mill to generate flakes. The flaked seed then undergoes a cooking process in which it is conveyed to a heated drum where the flakes are cooked at elevated temperatures (typically from 70-90° C.). The cooking helps to reduce the viscosity of the oil to allow for more efficient extraction in subsequent steps. Cooked seed flakes are then pressed in a series of screw presses or expellers which can remove 50-60% of the oil. Aside from the oil, which is removed for further processing, the pressing produces a meal cake that is ideal for solvent extraction. Using several cycles of extraction, the meal cake is treated with a solvent such as hexane to remove the residual oil from the meal. The meal is then transferred to a desolventizer-toaster where it is heated to remove remaining solvent; the final step of the process, called toasting, involves injection of steam into the meal to remove the last traces of solvent. The meal is then cooled and dried by blowing forced air through it. In some cases, the seed can also be processed using a cold press methodology which is similar to above except it does not involve the use of solvent to remove residual oil from the oil cake, resulting in a meal with much higher oil composition. In other cases, meal containing high levels of glucosinolates can be combined with other ingredients and formulated into pellets for use as a biofumigant (U.S. Publication No. 2008/0199451).

*Brassica carinata* plants can also be used commercially for biofumigation to reduce the population of disease-causing organisms in the soil. Typically, a field is seeded with *Brassica* plants early in the planting season, the plants are grown for a time, and the biomass is collected between flowering and before seed set. The plant biomass is then chopped to release the myrosinase enzyme and convert the glucosinolates in the plant biomass to isothiocyanates. The chopped biomass is tilled into the soil prior to seeding of a second crop.

Uses of *Brassica carinata* Hybrid Variety Nujet 400

In one aspect, the invention is direct to a method of producing a commercial crop, the method comprising planting seed of *Brassica carinata* variety Nujet 400, representative seed of said variety having been deposited under ATCC accession number PTA-127252, and growing the commercial crop.

In another aspect, the invention is further directed to a method for producing a Doubled Haploid (DH) variety comprising isolating a flower bud of the F1 hybrid plant, dissecting out a haploid microspore, placing the haploid microspore in culture, inducing the microspore to differentiate into an embryo and subsequently into a plantlet, identifying whether the plantlet contains a diploid chromosome number, wherein the diploid chromosome number occurred through chromosome doubling, and continuing to grow the plantlet if it contains a diploid chromosome number. In one embodiment, the diploid chromosome number is obtained by chemical or physical means. In another aspect the invention is directed to a plant, plant part, or seed of such Double Haploid variety produced from the F1 hybrid plant resulting from crossing *Brassica carinata* variety Nujet 400 with a different *Brassica carinata* plant, or from direct culture of an F1 plant constituting Nujet 400

In yet another aspect, the invention is directed to a method of producing a *Brassica carinata* variety having a desired trait, as well as seeds, plants and plant parts of such variety, by crossing a plant of *Brassica carinata* variety Nujet 400 with a plant of another species of the family Brassicaceae comprising the desired trait, producing F1 progeny plants using embryo rescue techniques to recover viable F1 plants or growing F1 seeds, self-pollinating the F1 plants that have the desired trait and carinata character, producing F2 plants using embryo rescue techniques to recover viable F2 plants or growing F2 seeds, self-pollinating the F2 plants that have the desired trait and carinata character, using embryo rescue techniques to recover viable F3 plants or growing F3 seeds to produce progeny plants, self-pollinating the progeny plants that have the desired trait and carinata character to produce further progeny plants, and selecting the progeny plants with the desired trait and carinata character. In some embodiments, the steps of producing progeny plants, self-pollinating, and selecting progeny plants having the desired trait and carinata character are repeated until the progeny plant has the desired trait and the physiological and/or morphological characteristics set forth in one or more of Tables 1, 2, 3, 4, 5, 6, 7, and 8, as determined at the 5% significance level, when grown in the same location under the same environmental conditions as variety Nujet 400. In some embodiments, the desired trait is selected from the group consisting of male sterility, disease resistance, fungal resistance, pest resistance, herbicide tolerance, abiotic stress tolerance, and altered metabolism. In other embodiments, the desired trait is herbicide tolerance and the herbicide is selected from, but not limited to, the group consisting of glyphosate, glufosinate, imidazolinones, and auxin analogues such as 2,4-D and dicamba.

In another aspect, the present invention is directed to a cell of a plant of a *Brassica carinata* variety having a desired trait, as well as seeds, plants and plant parts of such variety, by crossing a plant of *Brassica carinata* Nujet 400 with a plant of another species of the family Brassicaceae comprising the desired trait, producing F1 progeny plants using embryo rescue techniques to recover viable F1 plants or growing F1 seeds, self-pollinating the F1 plants that have the desired trait and carinata character, producing F2 plants using embryo rescue techniques to recover viable F2 plants or growing F2 seeds, self-pollinating the F2 plants that have the desired trait and carinata character, using embryo rescue techniques to recover viable F3 plants or growing F3 seeds to produce progeny plants, self-pollinating the progeny plants that have the desired trait and carinata character to produce further progeny plants, and selecting the progeny plants with the desired trait and carinata character. In some embodiments, the steps of producing progeny plants, self-pollinating, and selecting progeny plants having the desired trait and carinata character are repeated until the progeny plant has the desired trait and the physiological and/or morphological characteristics set forth in one or more of Tables 1, 2, 3, 4, 5, 6, 7, and 8, as determined at the 5% significance level, when grown in the same location under the same environmental conditions as variety Nujet 400. In some embodiments, the desired trait is selected from the group consisting of male sterility, disease resistance, fungal resistance, pest resistance, herbicide tolerance, abiotic stress tolerance, and altered metabolism. In other embodiments, the desired trait is herbicide tolerance and the herbicide is selected from, but not limited to, the group consisting of glyphosate, glufosinate, imidazolinones, and auxin analogues such as 2,4-D and dicamba.

Another aspect of the present invention is directed to a tissue culture of protoplasts or regenerable cells of the plant or plant part produced from the seed of *Brassica carinata* variety Nujet 400, as well as a *Brassica carinata* plant regenerated from the tissue culture the physiological and/or morphological characteristics set forth in one or more of Tables 1, 2, 3, 4, 5, 6, 7, and 8, as determined at the 5% significance level, when grown in the same location under the same environmental conditions as variety Nujet 400. The tissue may be selected from the group consisting of leaves, pollen, embryos, roots, root tips, pods, flowers, ovules, and stalks.

In other aspects, the present invention is directed to a cell of *Brassica carinata* variety designated Nujet 400, as well as to a plant or plant part, or a protoplast of a plant or plant part, produced from a seed of *Brassica carinata* variety designated Nujet 400. In some embodiments, the plant part is an ovule, a leaf, pollen, a seed, an embryo a root, a root tip, a pod, a flower, or a stalk. In other embodiments, the plant part is pollen or an ovule. In other embodiments, the present invention is directed to a cell, plant or plant part having the physiological and/or morphological characteristics set forth in one or more of Tables 1, 2, 3, 4, 5, 6, 7, and 8, as determined at the 5% significance level, when grown in the same location under the same environmental conditions as variety Nujet 400.

The present invention also includes a method of producing a *Brassica carinata* variety comprising a desired trait, as well as a plant, plant part, or seed of such variety, by introducing a nucleic acid construct conferring the desired trait into a *Brassica carinata* plant of variety Nujet 400 using polyethylene glycol (PEG) mediated uptake, electroporation, ballistic infiltration using DNA coated microprojectiles (gene gun), an *Agrobacterium* infiltration-based vector, or a plant virus-based vector. In some embodiments, the nucleic acid construct comprises a transgene. In other embodiments, the nucleic acid construct comprises an RNAi construct. In some embodiments, the *Brassica carinata* variety comprises the desired trait and the physiological and/or morphological characteristics set forth in one or more of Tables 1, 2, 3, 4, 5, 6, 7, and 8, as determined at the 5% significance level, when grown in the same location under the same environmental conditions as variety Nujet 400. In other embodiments, the desired trait is selected from the group consisting of male sterility, disease resistance, fungal resistance, pest resistance, herbicide tolerance, abiotic stress tolerance, and altered metabolism. In other embodiments, the desired trait is herbicide tolerance and the herbicide is selected from, but not limited to, the group consisting of glyphosate, glufosinate, imidazolinones, and auxin analogues such as 2,4-D and dicamba.

In another aspect, the invention is directed to the use of a plant of *Brassica carinata* variety Nujet 400 to produce a *Brassica carinata* variety comprising a new trait, wherein the new trait is introduced by exposing seedlings or microspores to a mutagenic agent. In some embodiments, the mutagenic agent is ethyl methanesulfonate, N-ethyl-N-nitrosourea, or x-ray, gamma or ultraviolet radiation.

In another aspect, the invention is directed to a cell of a plant of a *Brassica carinata* variety produced from variety Nujet 400, wherein the *Brassica carinata* variety comprises a new trait and is produced by a method comprising exposing seedlings or microspores to a mutagenic agent and allowing the surviving fraction to develop into mature plants. In some embodiments, the mutagenic agent is ethyl methanesulfonate, N-ethyl-N-nitrosourea, or x-ray, gamma or ultraviolet radiation.

In another aspect, the invention is directed to a method of producing a commercial crop of a *Brassica carinata* variety Nujet 400 or of a *Brassica carinata* variety produced by any of methods described herein. In another aspect, the invention is directed to a method of producing a commercial plant product from the commercial crop. In some embodiments, the commercial plant product comprises oil, meal, protein isolate, or biofumigant. In another aspect the invention is directed to a method of producing crushed, non-viable seed of *Brassica carinata* variety Nujet 400 or a *Brassica carinata* variety produced by any of methods described herein.

In another aspect, the invention is directed to a method of biofumigation comprising, growing a plant of *Brassica carinata* variety Nujet 400 or a *Brassica carinata* variety produced by any of methods described herein in a field, collecting the *Brassica carinata* plant biomass between flowering and seed set, chopping the biomass, and incorporating the chopped biomass into the soil.

The citation of any publication herein is not an admission that the publication is prior art with respect to the present application.

Although the foregoing invention has been described in some detail by way of illustration and example for purposes of clarity of understanding, it is readily apparent to those of ordinary skill in the art in light of the teachings of this invention that certain changes and modifications may be made thereto without departing from the scope of the appended claims.

It is to be understood that any numerical value inherently contains certain errors necessarily resulting from the standard deviation found in the respective testing measurements. Also, as used herein, the term “about” generally means within 10%, 5%, 1%, or 0.5% of a given value or range. Alternatively, the term “about” means within an acceptable standard error of the mean when considered by one of ordinary skill in the art. Unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

As used in this specification and the appended claims, the singular forms “a,” “an,” and “the” include plural reference unless the context clearly dictates otherwise. Unless defined otherwise all technical and scientific terms used herein have the same meaning as commonly understood to one of ordinary skill in the art to which this invention belongs.

The phrase “and/or,” as used herein in the specification and in the claims, should be understood to mean “either or both” of the elements so conjoined, i.e., elements that are conjunctively present in some cases and disjunctively present in other cases. Multiple elements listed with “and/or” should be construed in the same fashion, i.e., “one or more” of the elements so conjoined. Other elements may optionally be present other than the elements specifically identified by the “and/or” clause, whether related or unrelated to those elements specifically identified. Thus, as a non-limiting example, a reference to “A and/or B”, when used in conjunction with open-ended language such as “comprising” can refer, in one embodiment, to A only (optionally including elements other than B); in another embodiment, to B only (optionally including elements other than A); in yet another embodiment, to both A and B (optionally including other elements); etc.

As used herein in the specification and in the claims, “or” should be understood to encompass the same meaning as “and/or” as defined above. For example, when separating items in a list, “or” or “and/or” shall be interpreted as being inclusive, i.e., the inclusion of at least one, but also including more than one, of a number or list of elements, and, optionally, additional unlisted items.

As used herein, whether in the specification or the appended claims, the transitional terms “comprising”, “including”, “carrying”, “having”, “containing”, “involving”, and the like are to be understood as being inclusive or open-ended (i.e., to mean including but not limited to), and they do not exclude unrecited elements, materials or method steps. Only the transitional phrases “consisting of” and “consisting essentially of”, respectively, are closed or semi-closed transitional phrases with respect to claims and exemplary embodiment paragraphs herein. The transitional phrase “consisting of” excludes any element, step, or ingredient which is not specifically recited. The transitional phrase “consisting essentially of” limits the scope to the specified elements, materials or steps and to those that do not materially affect the basic characteristic(s) of the invention disclosed and/or claimed herein.

Characteristics of the *Brassica carinata* Hybrid Variety Nujet 400

The *Brassica carinata* hybrid variety Nujet 400 has shown uniformity and stability for all traits described in the variety description information in Table 7 below.

In embodiments, Nujet 400 may be grown as a late-maturing, non-food cover crop between primary crops. Nujet 400 provides the benefits of a typical cover crop (such as improved soil health, weed control, etc.) while also producing low carbon fuel feedstock, which serves as an extra source of income for farmers. An improvement for Nujet 400 over other carinata cover crop varieties evaluated to date is its superior yield potential in a lower nitrogen input, winter environment as tested in Argentina, Uruguay, and the Southern U.S.

Nujet 400 has a high level of heterozygosity as a hybrid variety between two distinct inbred parental lines, and a modest level of heterogeneity. The heterogeneity is mostly visually manifested in a low percentage of white petal colour types appearing in a yellow petal colour background.

A summary of characteristics of Nujet 400 is provided below:

Variety type: Hybrid

Pollination control system: Ogura

Environments targeted: Winter seasons in South America (Argentina, Uruguay) and the Southern United States (Georgia, Alabama, Northern Florida, North and South Carolina, Texas)

Key improvement(s):

1. Yield potential—Stably produces higher yields of approximately 25 to 30% greater than the current OP commercial variety, Avanza 641, in all target geographies Agronomic descriptors:

Plant height: 130 cm±10

Petal colour: Pale yellow; low level white petal (~10%)

Seed colour: Light brown

Plant structure: High branching, high biomass, large lower leaf size

Phenology—

Days to flower: Nuola 300 (Nuseed hybrid canola variety)+2 weeks; 100-120 days after planting Flowering duration: 4-5 weeks Days to maturity: Nuola 300 (Nuseed hybrid canola variety)+3 weeks; 170-180 days after planting Disease ratings: Blackleg (R); Sclerotinia (M)

Herbicide tolerance system: None (Conventional)

Seed quality descriptors:

Seed oil content: 44-45% (−1.6% vs. Avanza 641)

Total glucosinolate content: 75-80 μmol/g (+10 μmol/g vs. Avanza 641)

Erucic acid content: 40-42% (−3% vs. Avanza 641)

Whole seed protein content: 25-26% (Approximately equal to Avanza 641)

Total Sats: 6% or less (common to most Carinata varieties)

All seed quality estimates were based on whole seed analyzed at ≤5% seed moisture, and generated by NIR analysis using a *Brassica carinata* specific NIR calibration formula. Estimates are on dry seed basis.

EXAMPLES

Example 1

Field Trials

Winter trials were conducted during winter in Argentina, Uruguay, and southern states of the United States using best agronomic practices for carinata as described in the "Carinata Commercial Production Manual", 2021-22 Edition—Fall Planting, Winter Season Southern US, available from Nuseed Americas Inc., and "Carinata, The Sustainable Crop for a Bio-based Economy: 2021-2022 Production Recommendations for the Southeastern United States", published by University of Florida. Several newly developed carinata varieties, including Nujet 400, were grown in a Randomized Complete Block Design trial (RCBD), comprising 4 replicate plots (unless otherwise noted) along with plots of check varieties Avanza 641 and/or Nuola 300. During the trials, the experimental lines and check varieties were closely observed, and descriptions of phenotypic characteristics and agronomic traits were recorded. After plants had reached maturity, seed was collected for subsequent NIR based seed quality analysis (as described in the definitions section). In "head-to-head" trials, data collected for Nujet 400 and the check variety occur in the same trial.

Example 2

Characteristics of Nujet 400 Grown in Winter Trials in Southern U.S. and South America

*Brassica carinata* is an important winter crop in subtropical regions, where it is grown in in rotations with summer crops. Under such conditions, it is advantageous for carinata varieties to have agronomic traits such as the ability to withstand early and late season weather extremes in temperature and moisture.

Winter trials were conducted at several sites in Argentina, Uruguay, and Southern states of the United States, as described in Example 1, to assess characteristics of Nujet 400 such agronomic traits, seed yield and multi-year performance. Each characteristic was assessed as described in the DEFINITIONS section, above. Least square mean values from replicated data sets were calculated using the REML model and pairwise comparisons carried out using paired t-test (head-to-head analysis) at the 5% probability level, unless otherwise noted. All quantitative data analysis was carried out using Agrobase.

Earliness to maturity: data was collected for Nujet 400 and check varieties Nuola 300 and Avanza 641 based on eight separate trials carried out in Argentina and Uruguay in winter 2021. The results of the trials are shown below in Table 1.

TABLE 1

Hybrid trial maturity ratings - Eight trials in Argentina and Uruguay, winter 2021*

| Name | Type | Stage | Average rating (8 trials)** |
|---|---|---|---|
| Nuola 300 | HYB(NAP) | Canola Check | 1.0 |
| Nujet 400 | HYB | Hybrid Check | 3.7 |
| Avanza 641 | OP | OP Check | 3.9 |

*Trial sites in Argentina: Reconquista, Maria Juana, Venado, Tuerto, Paraná, Guerrico, Balcarce. Trial sites in Uruguay: La Estanzuela and Young.

**Earliness of maturity was rated on a scale of 1-5, where "1" is early and "5" is late.

Combined days to flower (DTF): data was collected for Nujet 400 and check varieties Nuola 300 and Avanza 641 based on seven separate trials carried out in Argentina during the winters of 2020 and 2021 The results of the trials are shown below in Table 2.

TABLE 2

Combined days to flower (DTF) analysis of Nujet 400 vs. Avanza 641 and Nuola 300 Hybrid trial maturity ratings - Seven trials in Argentina, winter 2020 and 2021*

| NAME | Median** | N | Letter*** |
|---|---|---|---|
| Avanza 641 | 104.26 | 19 | A |
| Nujet 400 | 103.16 | 19 | A |
| Nuola 300 | 90.95 | 19 | D |

*Trial sites: Paraná, 2020; Venado Tuerto, 2021; Balcarce, 2021; Guerrico, 2021; Paraná, 2021; and Reconquista, 2021.

**Medians that share a common letter are not significantly different from one another (p > 0.05). Test: Fisher's least significant difference test (LSD), alfa = 0.05, DMS – 1.53715.

Seed oil content: data was collected for seed oil content (% on dry basis) of Nujet 400 and check variety Avanza 641 in head-to-head trials. Trials were carried out at sites in South America and Southeastern U.S. The results of these trials are summarized below in Table 3.

TABLE 3

Seed oil content of Nujet 400 vs. Avanza 641 in trials carried out in South America and Southern United States

| Site | Nujet 400: oil % (on dry basis) | Avanza 641: oil % (on dry basis) | Difference | No. of trials | No. of seasons |
|---|---|---|---|---|---|
| South America | 44.9 | 47.4 | −2.5* | 12 | 4 |
| All trials[a] | 44.3 | 45.9 | −1.6*** | 27 | 6 |

[a]Combines all data from South America and Southern U.S. winter trials

Glucosinolate content: data was collected for glucosinolate content (μmol/g) of Nujet 400 and check varieties Nuola 300 and Avanza 641 based on head-to-head trials carried out in South America and South U.S. Glucosinolate (GSL) content was measured in μmol/g. Results of the trials are shown in Table 4 below.

TABLE 4

Glucosinolate oil content of Nujet 400 vs. Avanza 641 in head-to-head trials carried out in South America and Southern United States

| Site | Nujet 400: GSL (μmol/g) | Avanza 641: GSL (μmol/g) | Difference | No. of trials | No. of seasons |
|---|---|---|---|---|---|
| South America | 74 | 64 | +10** | 12 | 4 |
| All trials[a] | 79 | 73 | +6*** | 27 | 6 |

[a]Combines all data from South America and Southern U.S. winter trials
Analysis method = Paired t-test where Avanza 641 and hybrid occur in the same trial;
*P < 0.1,
**P < 0.05,
***P < 0.01

Seed protein content: data was collected for seed protein content (%) of Nujet 400 and check varieties Nuola 300 and Avanza 641 based on head-to-head trials carried out in South America and Southern United States. The results are summarized below in Table 5.

TABLE 5

Seed protein content of Nujet 400 vs. Avanza 641 in head-to-head trials carried out in South America and Southern United States

| Site | Nujet 400: (%) | Avanza 641: (%) | Difference | No. of trials | No. of seasons |
|---|---|---|---|---|---|
| South America | 25.4 | 25.3 | +0.1 | 12 | 5 |
| All trials[a] | 24.9 | 25.5 | −0.6* | 27 | 6 |

[a]Combines all data from South America and Southern U.S. winter trials
Analysis method = Paired t-test where Avanza 641 and hybrid occur in the same trial;
*P < 0.1,
**P < 0.05,
***P < 0.01

Seed yield: data was collected for seed yield (kg/ha) of Nujet 400 and check variety Avanza 641 based on head-to-head trials carried out in South America and Southern United States. The results are summarized below in Table 6.

TABLE 6

Seed oil content of Nujet 400 vs. Avanza 641 in head-to-head trials carried out in winter trials in South America and Southern United States

| Site | Nujet 400: seed yield (kg/ha) | Avanza 641: seed yield (kg/ha) | Nujet 400 yield as % of Avanza 641 | No. of trials | No. of seasons | Significance |
|---|---|---|---|---|---|---|
| South America | 3653 | 2797 | **134.9** | 12 | 5 | +++ |
| All trials[a] | 3228 | 2478 | **130.3** | 27 | 6 | +++ |

[a]Combines all data from South America and Southern U.S. winter trials
Analysis method = Paired t-test where Avanza 641 and hybrid occur in the same trial;
*P < 0.1,
**P < 0.05,
***P < 0.01

Resilience to frost: data was collected for Nujet 400 and check varieties Nuola 300 and Avanza 641 based on trials carried out during the winter of 2021 at three different sites in Argentina: Maria Juana, Venado Tuerto, and Guerrico. Resilience to frost was rated on a scale of 1 to 7, where "7" is no damage and "1" is severe damage. The frost resilience rating for Nujet 400 was 4.8, as compared 3.3 for Avanza and 5.3 for Nuola 300. Thus, the frost resilience rating for Nujet 400 is notably improved as compared to Avanza.

A summary of data for several key characteristics of Nujet 400 vs. Avanza 641 collected from all winter trials carried out in the Southern United States and South America is provided below in Table 7.

TABLE 7

Summary of key characteristics of Nujet 400 vs. Avanza 641 in winter environment trials carried out in the Southern United States and South America

| | Nujet 400 | Avanza 641 | Difference | % of Avanza 641 | No. trials | No. years |
|---|---|---|---|---|---|---|
| Yield (kg/ha) | 3228 | 2478 | **+750**** | **130.3**** | 27 | 6 |
| Days to Maturity (DTM) | 172 | 173 | −1 day | — | 6 | 1 |
| Erucic acid (%) | 40.9 | 44.1 | −3.2 | 92.7 | 27 | 6 |
| Protein (%) | 24.9 | 25.5 | −0.6 | 97.6 | 27 | 6 |
| Oil (%) | 44.3 | 45.9 | −1.6 | 96.5 | 27 | 6 |
| Total GSL (μmol/g) | 79 | 73 | +6 | 108.2 | 27 | 6 |
| Frost rating (1-7) | 4.8 | 3.3 | **+1.5** | — | 3 | 1 |

*Reported data is from head-to-head analysis where Avanza 641 and hybrid variety appeared in the same trial
**Bold highlight is primary selection trait for variety The *Brassica carinata* variety Nujet 400 has shown uniformity and stability for all traits described in the variety description information in Table 7.

As can be seen from the data presented above, under the growth conditions of the trials, *Brassica carinata* variety Nujet 400 and the check variety Avanza 641 had very similar phenology and biomass profiles, and they produced seeds of similar quality (such as wt % oil content). However, as compared to the check variety Avanza 641, Nujet 400 produced a significantly increased yield of seed per hectare of land (as measured by kg of seed produced per hectare of land). Nujet 400 also demonstrated a higher resilience to frost as compared to Avanza 641.

Based on these findings, the Nujet 400 variety may be a suitable candidate for commercial exploitation in the winter seasons in South America (e.g., Argentina, Uruguay) and the Southern United States (e.g., Georgia, Alabama, Northern Florida, North and South Carolina, Texas), and possibly other geographical regions, in particular for the production of biofuel.

Example 3

Phenology and Physiology of Nujet 400 Grown in Buenos Aires, Argentina

Small plot field trials were carried out at the School of Agriculture, University of Buenos Aires (34°36'S 58°26'W) in winter 2021, in order to study the phenology and physiology of Nujet 400 as compared to check variety Avanza 641.

Nujet 400 (hybrid) and Avanza (OP variety) with 5 replicates were sown on Jun. 23, 2021 at a planting rate of 100 plants/$m^2$. Soil type: typical Argiudoll with a strong clayey horizon (Bt) at 40 cm depth. Husbandry: irrigated and fertilized (up to 100 kg N available/ha) and preventive fungicide in VE and V6. Meteorological conditions: Buenos Aires has a humid subtropical climate. During the winter of 2021, mean temperatures were about 12° C. in June (at time of sowing), increasing to a mean of 22° C. by November, with a few days with temperature lows close to freezing prior to flowering and temperature highs >30° C. during grain filling. The region was experiencing a La Niña event in the winter of 2021 and therefore the winter was initially drier than historical records (supplemental irrigation was used) with heavy rains at late November prior to maturity. Crop phenology: There was similar crop phenology in both genotypes (for sowing in late June). Beginning of flowering occurred in mid-September (Nujet: September 19; Avanza: September 17). Maturity was achieved in late November (November 30) for both genotypes. Whole crop cycle: 160 days after sowing (around 55% of cycle for pre-flowering and 45% for post-flowering).

Canopy light interception: Soil coverage for both varieties increased quickly from 30 to 60 days after emergence (DAE), from 10% at 30 DAE to 90% at 60 DAE. Light capture efficiency for both genotypes was >90% by early September. Canopy light interception was slightly higher for Nujet 400; for example, canopy light interception was >95% for Nujet 400 and >90% for Avanza 641 when measured September 14 (73 DAE).

Aerial biomass: Both genotypes showed a typical sigmoid pattern for development of aerial biomass, with only ⅓ of the aerial biomass growth appearing before flowering and the remaining ⅔ appearing after flowering. Both genotypes reached similar aerial biomass when harvested at 150 DAE (Nujet 400: 98313±1076 kg/ha; Avanza 641: 8943±1437 kg/ha). There was similar biomass allocation in both genotypes, with most of the biomass being in the branches (45%) and the main stem (35%) at 131-146 DAE.

Root structure and length: Samples of 12.5 kg per plot were taken at a first depth of 0-200 cm (10 kg) and at second depth of 200-400 cm deep (2.5 kg). The samples were soaked in saline overnight to disperse soil, then cleaned by hand by a trained technician. Root structure was similar for both genotypes at the beginning of flowering around 80-86 DAE: heavy, long taproots, shallow lateral roots (at 90), and an abundance of fine, bright root hairs. For both genotypes, a reduction in the number of root hairs was observed after maturity at 166 DAE (fewer root hairs observed). Total root length was about 1 km per m 2 of soil for both genotypes at beginning of flowering (80-86 DAE) and decreased post-flowering to about 0.6-0.8 km per $m^2$ at maturity (166 DAE). Roots were mainly in the topsoil and did not extend beyond 0.4 m, due to the strong Bt clay horizon.

Root biomass: At flowering, 800-1000 kg/ha of dry biomass was allocated in the roots and this amount did not increase or decrease significantly between flowering and maturity. As a result, the ratio of root biomass to aerial biomass at flowering was 0.21 for Nujet 400 and 0.33 for Avanza 641, and decreased to 0.1 for Nujet 400 and 0.12 for Avanza 641 at maturity. Root biomass is useful to calculate carbon sequestering.

Canopy structure at harvest: Five plants from each plot (25 plants in total for genotype) were randomly selected to measure canopy structure. Characteristics of canopy structure are summarized below in Table 8. Notably, Nujet 400 had significantly more siliques on the main raceme, less branching, and the first siliques were located taller in the canopy respect to Avanza 641.

TABLE 8

Canopy structure of Nujet 400 and Avanza 641

| Canopy structure | Nujet 400 | Avanza 641 | p-value |
|---|---|---|---|
| Plant height (cm) | 150 ± 3.6 | 141 ± 3.2 | 0.0890 |
| Main raceme length (cm) | 31 ± 1.2 | 29 ± 0.5 | 0.0822 |
| Height to the first siliques (cm) | 108 ± 2.6 | 89 ± 3.0 | 0.0011* |
| Number of primary branches | 5.7 ± 0.4 | 6.9 ± 0.3 | 0.0252* |
| Number of siliques from the main raceme | 16 ± 0.5 | 12 ± 0.4 | 0.0008** |

Statistically significant:
*P < 0.05,
**P < 0.01

The overall phenology and physiology of Nujet 400 was found to be very similar to Avanza 641 when grown under the same conditions. Consequently, it is expected that Nujet 400 will provide similar benefits as a cover crop as regards metrics such as: weed management; reduction of wind and water erosion; soil health improvement through build up of organic matter; and soil tilth and loosening through extensive root systems. Notably, Nujet 400 and Avanza 641 both have high plant biomass, which is a desirable trait for a cover crop.

Example 4

Morphology of Nujet 400 Grown in Canada

Morphology was assessed for Nujet 400 grown in a Canadian environment using best agronomic practices for carinata for the Northern Plains. However, the general observations on the morphology of Nujet 400 provided below hold true across growing regions.

Colour of siliques: purple coloration was observed on siliques on main racemes.

Number of siliques: the secondary branches had about double the number of siliques as compared to the main raceme.

Secondary racemes: there was an average of 15 seeds per silique, which is in line with observations from trials carried out at other sites.

Petal colour: pale yellow; there is a low level of white petals (about 10%).

Seed colour: light brown.

Plant structure: High branching, large lower leaf size.

The following observations are from a single plant, but they appear to be representative of the majority of plants in plots:

Nine pod bearing secondary racemes plus main raceme (ten pod bearing racemes total).

Total of 16 seed-bearing siliques on the main raceme.

Number of seed-bearing siliques on secondary branches: 42, 52, 28, 52, 32, 20, 34, 27, and 23. Average=34 siliques per raceme; St Dev=11.8.

Number of seeds per silique from main raceme: 18, 14, 14, 12, 19, 18, 14, 14, 16, 13, 14, 15, 19, 16, 14, 10. Average=15 seeds per silique; St Dev=2.5.

Notably, the number of seed-bearing siliques on the main raceme is consistent with observations made in Experiment 3.

Deposit

Applicant(s) have made a deposit of at least 2500 seeds of *Brassica carinata* variety Nujet 400 with the American Type Culture Collection (ATCC®), P.O. Box 1549 Manassas, VA 20110 USA, Tel. (800) 638-6597 or 703-365-2700, Fax: 703-365-2750, under accession number PTA-127252. The seeds deposited with ATCC on Jan. 14, 2022 for Nujet 400 were taken from the seed stock maintained by Nuseed Global Innovation Ltd, since prior to the filing date of this application. The deposit was accepted and viability of the deposit was confirmed on Jun. 15, 2022. The deposit of seed of *Brassica carinata* variety Nujet 400 will be maintained in the ATCC depository, which is a public depository, for a period of 30 years, or 5 years after the most recent request, or for the enforceable life of the patent, whichever is longer, and will be replaced if it becomes nonviable during that period. Additionally, Applicant has satisfied all the requirements 37 C.F.R. § 1.801-1.809, including providing an indication of the viability of the sample upon deposit. Applicant imposes no restrictions on the availability of the deposited material from ATCC; however, Applicant has no authority to waive any restrictions imposed by law on the transfer of biological material or its transportation in commerce. Applicant(s) do not waive any infringement of their rights granted under this patent or rights applicable to *Brassica carinata* variety Nujet 400 under the Plant Variety Protection Act (7 USC 2321 et seq.).

BREEDING HISTORY

Nujet 400 is a hybrid variety derived from two inbred parental lines. This hybrid makes use of the Ogura pollination control system, having an R line (male), A line (male sterile female), and B line (maintainer, same genetic background as A line).

Male parent: The restorer or male line is 6076, a shorter stature, shorter cycle length, white petal colour line. 6076 pedigree: The Rfo gene donor was VR07-358, a *Brassica juncea* breeding line, which was crossed with a *Brassica carinata* line 080793EM as the male parent. Four consecutive backcross rounds were done using *carinata* breeding lines as the male parent, and tracing the presence of the Rfo gene using molecular markers through each breeding cycle. A BC4 line was self-pollinated to generate several self-pollinated BC4F2 progeny, and 6076 was selected from among these progenies as a *Brassica carinata* background in which the Rfo gene was stably introgressed.

Female parent: The A line is AGR044-3111. AGR044-3111 is an OP variety derived from six rounds of single plant selection from nursery rows, in which the primary criteria were suitable agronomic look, and selections containing high oil content and reduced total glucosinolate content in the seed. These selections originated from an initial accession derived from the Plant Gene Resources of Canada (PGRC) collection, CN 101659. This was followed by two cycles of tent isolations where off-type plants were removed, such as plants with white petal colour, to increase uniformity of the variety. Finally, a 1 ha field isolation increase was done where white petal colour plants, and plants with deep purple colour stems, were removed. This formed the source of the B line seed which is being used in seed production of Nujet 400. AGR044-3111 has a low level of heterogeneity and heterozygosity, most visibly evidenced by a small percentage of white petal colour off-types in a primarily yellow petal colour population.

REFERENCES

Alcántara, C., et al. (2011). "Management of cruciferous cover crops by mowing for soil and water conservation in southern Spain." *Agricultural Water Management* 98 (6): 1071-1080.

Angus, J., et al. (2011). A review of break-crop benefits of brassicas. *17th Australian Research Assembly on Brassicas, Wagga Wagga, NSW, August* 2011. Wagga Wagga, NSW, NSW DPI: 123-127.

Babic, V., et al. (1998). "Development of an efficient Agrobacterium-mediated transformation system for *Brassica carinata.*" *Plant Cell Reports* 17 (3): 183-188.

Bannerot, H., et al. (1977). "Unexpected Difficulties Met With The Radish Cytoplasm In *Brassica oleracea.*" *Cruciferae Newsl* 2:1.

Barro, F. and Martin, A. 1999, Response of different genotypes of *Brassica carinata* to microspore culture, Plant Breeding 118 (1): 79-81

Bevan, M. (1984). "Binary Agrobacterium vectors for plant transformation." *Nucl. Acids Res.* 12 (22): 8711-8721.

Black, C. K. and J. F. Panozzo (2004). "Accurate Technique for Measuring Color Values of Grain and Grain Products Using a Visible-NIR Instrument." *Cereal Chemistry* 8 (14): 469-474.

Bouaid, A., et al. (2005). "Pilot plant studies of biodiesel production using *Brassica carinata* as raw material." *Catalysis Today* 106 (1-4): 193-196.

Cardone, M., et al. (2003). "*Brassica carinata* as an alternative oil crop for the production of biodiesel in Italy: agronomic evaluation, fuel production by transesterification and characterization." *Biomass and Bioenergy* 25 (6): 623-636.

Cardone, M., et al. (2002). "*Brassica carinata* as an alternative oil crop for the production of biodiesel in Italy: engine performance and regulated and unregulated exhaust emissions." *Environ Sci Technol* 36 (21): 4656-4662.

Cheng, B., et al. (2010). "Towards the production of high levels of eicosapentaenoic acid in transgenic plants: the effects of different host species, genes and promoters." *Transgenic Research* 19 (2): 221-229.

Datla, R. S., et al. (1992). "Modified binary plant transformation vectors with the wild-type gene encoding NPTII." *Gene* 122 (2): 383-384.

Delourme, R., et al. (1991). *Radish cytoplasmic male sterility in rapeseed: breeding restorer lines with a good female fertility*. Eighth International Rapeseed Congress, Saskatoon, Canada.

Delourme, R., et al. 1998). "Characterisation of the radish introgression carrying the Rfo restorer gene for the Ogu-INRA cytoplasmic male sterility in rapeseed (*Brassica napus* L.)." *Theor. Appl. Genet.* 97 (1-2): 129-134.

Drenth, A. C., et al. (2015). "Fuel property quantification of triglyceride blends with an emphasis on industrial oilseeds camelina, carinata, and pennycress." *Fuel* 153: 19-30.

Finer, J. J., et al. (1999). "Particle bombardment mediated transformation." *Curr Top Microbiol Immunol* 240: 59-80.

Fromm, M., et al. (1985). "Expression of genes transferred into monocot and dicot plant cells by electroporation." *Proc. Natl. Acad. Sci. USA* 82 (17): 5824-5828.

Gasol, C., et al. (2007). "Life cycle assessment of a *Brassica carinata* bioenergy cropping system in southern Europe." *Biomass and Bioenergy* 31 (8): 543-555.

Gasol, C. M., et al. (2009). "Feasibility assessment of poplar bioenergy systems in the Southern Europe." *Renewable and Sustainable Energy Reviews* 13 (4): 801-812.

Gesch, R. W., et al. 2015). "Comparison of several Brassica species in the north central U.S. for potential jet fuel feedstock." *Industrial Crops and Products* 75b: 2-7.

Getinet, A., et al. (1996). "Agronomic performance and seed qualilty of Ethiopian mustard in Saskatchewan." *Canadian J. Plant Science* 76 (3): 87-392.

Getinet, A., G. Rakow, J. P. Raney And R. K. Downey (1997). "Glucosinolate content in interspecific crosses of *Brassica carinata* with *B. juncea* and *B. napus." Plant Breeding* 116 (1): 39-46.

Gleba, Y., S. Marillonnet and V. Klimyuk (2004). "Engineering viral expression vectors for plants: the 'full virus' and the 'deconstructed virus' strategies." *Curr Opin Plant Biot* 7 (2): 182-188.

Heyn, F. W. (1976). "ransfer of restorer genes from Raphanus to cytoplasmic male sterile *Brassica napus." Cruciferae Newsl* 1: 15-16.

Heyn, F. W. (1978). "Cytoplasmic Genetic-Male Sterility in *Brassica Napus." Cruciferae Newsl* 3: 34-35.

Impallomeni, G., et al. (2011). "Synthesis and characterization of poly(3-hydroxyalkanoates) from *Brassica carinata* oil with high content of erucic acid and from very long chain fatty acids." *Int. J. Biol. Macromol.* 48 (1): 137-145.

Jadhav, A., et al. (2005). "Increased levels of erucic acid in *Brassica carinata* by co-suppression and antisense repression of the endogenous FAD2 gene." *Metab Eng* 7 (3): 215-220.

Jeffs, K. A., Ed. (1978). *Seed treatment/compiled and edited by K. A. Jeffs*. Monographs (Collaborative International Pesticides Analytical Council); 2. Harpenden: Cambridge (King's Hedges Rd, Cambridge CB4 2PQ), Collaborative International Pesticides Analytical Council; [Distributed by] Heffers Printers Ltd.

Johnson, C. M., et al. (1989). "Direct gene transfer via polyethylene glycol." *Methods in Cell Science* 12 (4): 127-133.

Kirkegaard, J. A. and M. Sarwar (1998). "Biofumigation potential of brassicas." *Plant and Soil* 201 (1): 71-89.

Lazzeri, L., et al. (2009). "On Farm Agronomic and First Environmental Evaluation of Oil Crops for Sustainable Bioenergy Chains." *Ital. J. Agron./Riv. Agron.* 4: 171-180.

Márquez-Lema, A., et al. (2008). "Development and characterisation of a *Brassica carinata* inbred line incorporating genes for low glucosinolate content from *B. juncea." Euphytica* 164 (2): 365-375.

Meier, U., et al. (2009). "The BBCH system to coding the phenological growth stages of plants—history and publications—." *Journal Für Kulturpflanzen* 61 (2): 41-52.

Miki, B. L., et al. (1990). "Transformation of *Brassica napus* canola cultivars with *Arabidopsis thaliana* acetohydroxyacid synthase genes and analysis of herbicide resistance." *Theor Appl Genet* 80 (4): 449-458.

Mnzava, N. A. & Schippers, R. R., 2007. *Brassica carinata* A. Braun. [Internet] Record from PROTA4U. van der Vossen, H. A. M. & Mkamilo, G. S. (Editors). PROTA (Plant Resources of Tropical Africa/Ressources végétales de l'Afrique tropicale), Wageningen, Netherlands.

Mourato, M. P., et al. (2015). "Effect of Heavy Metals in Plants of the Genus *Brassica." Int J Mol Sci* 16 (8): 17975-17998.

Nagaharu, U. (1935). "Genome analysis in *Brassica* with special reference to the experimental formation of *B. napus* and peculiar mode of fertilization." *Japanese Journal of Botany* 7: 389-452.

Neugart, S., et al. (2017). "Indigenous leafy vegetables of Eastern Africa—A source of extraordinary secondary plant metabolites." *Food Research International* 100: 411-422.

Newman, Y. C., et al. (2010 (revised)). Cover Crops. I. Extension and U. o. Florida.

Newson, W. R., et al. (2014). "Effect of additives on the tensile performance and protein solubility of industrial oilseed residual based plastics." *J Agric Food Chem* 62 (28): 6707-6715.

Ogura, H. (1968). "Studies on the New Male-Sterility in Japanese Radish, with Special Reference to the Utilization of this Sterility towerds the Practical Raising of Hybrid Seeds." *Memoirs of the Faculty of Agriculture, Kagoshima University* 6 (2): 39-78.

Pane, C., et al. (2013). "Screening of plant-derived antifungal substances useful for the control of seedborne pathogens." *Archives of Phytopathology and Plant Protection* 46 (13): 1533-1539.

Pellan-Delourme, R. and M. Renard (1988). "Cytoplasmic male sterility in rapeseed (*Brassica napus* L.): female fertility of restored rapeseed with "Ogura" and cybrids cytoplasms." *Genome* 30 (2): 234-238.

Pelletier, G., et al. (1983). "Intergeneric cytoplasmic hybridization in cruciferae by protoplast fusion." *Molecular and General Genetics MGG* 191 (2): 244-250.

Pelletier, G., et al. (1987). Molecular, phenotypic and genetic characterization of mitochondrial recombinants in rapeseed. *Seventh International Rapeseed Conference:* 113-118.

Petolino, J. F., et al. (2010). "Zinc finger nuclease-mediated transgene deletion." *Plant Molecular Biology* 73 (6): 617-628.

Prakash, S., et al. (2011). History, Evolution, and Domestication of Brassica Crops. *Plant Breeding Reviews*, John Wiley & Sons, Inc.: 19-84.

Primard-Brisset, C., et al. (2005). "A new recombined double low restorer line for the Ogu-INRA cms in rapeseed (*Brassica napus* L.)." *Theor. Appl. Genet.* 111 (4): 736-746.

Rahman, M. and Tahir. M (2010) Inheritance of seed coat color of Ethiopian mustard (*Brassica carinata* A. Braun), Can. J. Plant Sci. 90(3): 279-281

Rothstein, S. J., et al. (1987). "Promoter cassettes, antibiotic-resistance genes, and vectors for plant transformation." *Gene* 53 (2): 153-161.

Sauer, N. J., et al. (2016). "Oligonucleotide-Mediated Genome Editing Provides Precision and Function to Engineered Nucleases and Antibiotics in Plants." *Plant Physiol* 170 (4): 1917-1928.

Seepaul, R., et al. (2015). Carinata, the Jet Fuel Cover Crop: 2016 Production Recommendations for the Southeastern United States. Agronomy Department, IFAS Extension and U. o. Florida, University of Florida. SS-AGR-384: 1-8.

Sherwani, S. I., et al. (2015). Modes of Action of Different Classes of Herbicides. *Herbicides, Physiology of Action, and Safety*. A. Price, J. Kelton and L. Sarunaite. Rijeka, InTech: Ch. 08.

Tang, G. and G. Galili (2004). "Using RNAi to improve plant nutritional value: from mechanism to application." *Trends Biotechnol* 22 (9): 463-469.

Taylor, D. C., et al. (2010). "*Brassica carinata*—a new molecular farming platform for delivering bio-industrial oil feedstocks: case studies of genetic modifications to improve very long-chain fatty acid and oil content in seeds." *Biofuels, Bioproducts and Biorefining* 4 (5): 538-561.

Thompson, C. J., et al. (1987). "Characterization of the herbicide-resistance gene bar from *Streptomyces hygroscopicus.*" *The EMBO Journal* 6 (9): 2519-2523.

Tian, E., et al. (2014). "Molecular marker-assisted breeding for improved Ogura cms restorer line (RfoRfo) and mapping of the restorer gene (Rfo) in *Brassica juncea.*" *Molecular Breeding* 34 (3): 1361-1371.

Warwick, S. I., et al. (2009). Guide to Wild Germplasm of Brassica and Allied Crops (tribe Brassiceae, Brassicaceae): 302.

Wohlleben, W., et al. (1988). "Nucleotide sequence of the phosphinothricin N-acetyltransferase gene from Streptomyces viridochromogenes Tu494 and its expression in Nicotiana tabacum." *Gene* 70 (1): 25-37.

Woo, J. W., et al. (2015). "DNA-free genome editing in plants with preassembled CRISPR-Cas9 ribonucleoproteins." *Nat Biotechnol* 33 (11): 1162-1164.

Xin, H. and Yu, P. (2014) Rumen degradation, intestinal and total digestion characteristics and metabolizable protein supply of carinata meal (a non-conventional feed resource) in comparison with canola meal., Animal Feed Sci Technol. 191: 106-110

Zanetti, F., et al. (2013). "Challenges and opportunities for new industrial oilseed crops in EU-27: A review." *Industrial Crops and Products* 50: 580-595.

Zanetti, F., et al. (2009). "Yield and oil variability in modern varieties of high-erucic winter oilseed rape (*Brassica napus* L. var. oleifera) and Ethiopian mustard (*Brassica carinata* A. Braun) under reduced agricultural inputs." *Industrial Crops and Products* 30 (2): 265-270.

The invention claimed is:

1. A hybrid *Brassica carinata* variety Nujet 400, representative seed of said variety having been deposited under ATCC accession number PTA-127252.

2. A seed of the *Brassica carinata* variety Nujet 400 of claim 1.

3. A plant or plant part of the *Brassica carinata* variety Nujet 400 of claim 1.

4. A method of producing a commercial crop, the method comprising planting seed of the *Brassica carinata* variety Nujet 400 of claim 1, and growing the commercial crop.

5. A *Brassica carinata* plant or plant part having the physiological and morphological characteristics of *Brassica carinata* variety Nujet 400, representative seed of variety Nujet 400 having been deposited under ATCC accession number PTA-127252.

6. A method for producing a Double Haploid variety comprising:

isolating a flower bud of the plant of claim 3;

dissecting out a haploid microspore;

placing the haploid microspore in culture;

inducing the microspore to differentiate into an embryo and subsequently into a plantlet;

identifying whether the plantlet contains a diploid chromosome number, wherein the diploid chromosome number occurred through chromosome doubling; and continuing to grow the plantlet if it contains a diploid chromosome number.

7. A cell of a *Brassica carinata* plant or plant part of claim 3.

8. A tissue culture of protoplasts or regenerable cells of the cell of claim 7.

9. The tissue culture of protoplast or regenerable cells of claim 8, wherein the protoplasts or regenerable cells are produced from a tissue selected from the group consisting of leaves, pollen, embryos, roots, root tips, pods, flowers, ovules, and stalks.

10. A *Brassica carinata* plant regenerated from the tissue culture of claim 8, wherein the plant has all the physiological and morphological characteristics of variety Nujet 400, representative seed of variety Nujet 400 having been deposited under ATCC accession number PTA-127252.

11. A method of producing a commercial plant product comprising growing the plant of claim 5 to produce a commercial crop and producing the commercial plant product from the commercial crop.

12. A method of producing a commercial plant product comprising growing the plant of claim 3 to produce a commercial crop and producing the commercial plant product from the commercial crop.

13. A product produced from a *Brassica carinata* plant of variety Nujet 400 of claim 1, wherein said product comprises at least one cell of said *Brassica carinata* plant of variety Nujet 400.

14. A product produced from the *Brassica carinata* plant of claim 5, wherein said product comprises at least one cell of said *Brassica carinata* plant of claim 5.

* * * * *